United States Patent
Simpson-Abelson et al.

(10) Patent No.: US 11,220,670 B2
(45) Date of Patent: *Jan. 11, 2022

(54) REMNANT TUMOR INFILTRATING LYMPHOCYTES AND METHODS OF PREPARING AND USING THE SAME

(71) Applicant: Iovance Biotherapeutics, Inc., San Carlos, CA (US)

(72) Inventors: Michelle R. Simpson-Abelson, Lithia, FL (US); Christopher Mosychuk, St. Petersburg, FL (US); Michael T. Lotze, Pittsburgh, PA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/180,200

(22) Filed: Feb. 19, 2021

(65) Prior Publication Data

US 2021/0189339 A1    Jun. 24, 2021

Related U.S. Application Data

(63) Continuation of application No. 16/462,056, filed as application No. PCT/US2017/062219 on Nov. 17, 2017.

(60) Provisional application No. 62/460,441, filed on Feb. 17, 2017, provisional application No. 62/423,750, filed on Nov. 17, 2016.

(51) Int. Cl.
| | |
|---|---|
| *C12N 5/0783* | (2010.01) |
| *A61P 35/00* | (2006.01) |
| *A61K 31/661* | (2006.01) |
| *A61K 35/17* | (2015.01) |
| *A61K 38/20* | (2006.01) |
| *A61K 39/00* | (2006.01) |

(52) U.S. Cl.
CPC .......... *C12N 5/0638* (2013.01); *A61K 31/661* (2013.01); *A61K 35/17* (2013.01); *A61K 38/2013* (2013.01); *A61K 39/0011* (2013.01); *A61P 35/00* (2018.01); *A61K 2039/5158* (2013.01); *C12N 2501/06* (2013.01); *C12N 2501/065* (2013.01); *C12N 2501/2302* (2013.01); *C12N 2501/2304* (2013.01); *C12N 2501/2307* (2013.01); *C12N 2501/2315* (2013.01); *C12N 2501/2321* (2013.01); *C12N 2501/515* (2013.01); *C12N 2501/599* (2013.01); *C12N 2501/998* (2013.01)

(58) Field of Classification Search
CPC ..... C12N 5/0638; A61P 35/00; A61K 31/661; A61K 35/17; A61K 38/2013; A61K 39/0011
See application file for complete search history.

(56) References Cited

U.S. PATENT DOCUMENTS

| | | | |
|---|---|---|---|
| 5,126,132 A | 6/1992 | Rosenberg | |
| 5,443,983 A | 8/1995 | Ochoa et al. | |
| 6,352,694 B1 | 3/2002 | June et al. | |
| 6,534,055 B1 | 3/2003 | June et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 7,144,575 B2 | 12/2006 | June et al. | |
| 7,175,843 B2 | 2/2007 | June et al. | |
| 7,232,566 B2 | 6/2007 | June et al. | |
| 7,479,269 B2 | 1/2009 | June et al. | |
| 7,572,631 B2 | 8/2009 | Berenson et al. | |
| 7,943,743 B2 | 5/2011 | Korman et al. | |
| 7,951,365 B2 | 5/2011 | Winqvist et al. | |
| 8,007,785 B2 | 8/2011 | Winqvist et al. | |
| 8,008,449 B2 | 8/2011 | Korman et al. | |
| 8,034,334 B2 | 10/2011 | Dudley et al. | |
| 8,206,702 B2 | 6/2012 | Winqvist et al. | |
| 8,211,424 B2 | 7/2012 | Winqvist et al. | |
| 8,211,425 B2 | 7/2012 | Winqvist et al. | |
| 8,617,884 B2 | 12/2013 | Berenson et al. | |
| 9,074,185 B2 | 7/2015 | Dudley et al. | |
| 9,476,028 B2 | 10/2016 | Karlsson-Parra et al. | |
| 9,528,088 B2 | 12/2016 | Berenson et al. | |
| 9,687,510 B2 | 6/2017 | Borrello et al. | |
| 9,844,569 B2 | 12/2017 | Gros et al. | |
| 10,172,887 B2 | 1/2019 | Borrello et al. | |
| 2005/0106717 A1 | 5/2005 | Wilson et al. | |

(Continued)

FOREIGN PATENT DOCUMENTS

| | | |
|---|---|---|
| CN | 106244538 A | 12/2016 |
| CN | 106591232 A | 4/2017 |

(Continued)

OTHER PUBLICATIONS

Prieto et al. "Enrichment of CD8+ Cells From Melanoma Tumor-infiltrating Lymphocyte Cultures Reveals Tumor Reactivity for Use in Adoptive Cell Therapy", J Immunother. Jun. 2010;33(5):547-56. (Year: 2010).*

(Continued)

*Primary Examiner* — Sharon X Wen
*Assistant Examiner* — Peter Johansen
(74) *Attorney, Agent, or Firm* — Morgan, Lewis & Bockius LLP

(57) ABSTRACT

In some embodiments, methods of delivering a therapeutically effective amount of an expanded number of tumor infiltrating lymphocytes obtained from tumor remnants to a patient in need thereof, for the treatment of a cancer, are disclosed.

18 Claims, 16 Drawing Sheets

Specification includes a Sequence Listing.

(56) References Cited

U.S. PATENT DOCUMENTS

| | | |
|---|---|---|
| 2011/0052530 A1 | 3/2011 | Dudley et al. |
| 2011/0136228 A1 | 6/2011 | Vera et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2014/0377739 A1 | 12/2014 | Welch et al. |
| 2015/0175966 A1 | 6/2015 | Vera et al. |
| 2015/0320798 A1 | 11/2015 | Borrello et al. |
| 2016/0010058 A1 | 1/2016 | Gros et al. |
| 2016/0208216 A1 | 7/2016 | Vera et al. |
| 2016/0215262 A1 | 7/2016 | Powell |
| 2017/0044496 A1 | 2/2017 | Sarnaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |
| 2018/0148690 A1 | 5/2018 | Gros et al. |
| 2018/0187150 A1 | 7/2018 | De Larichaudy |
| 2019/0000070 A1 | 1/2019 | De Larichaudy |
| 2019/0062706 A1 | 2/2019 | Almaasbak et al. |
| 2019/0136186 A1 | 5/2019 | Germeroth et al. |
| 2019/0276802 A1 | 9/2019 | Simpson-Abelson et al. |

FOREIGN PATENT DOCUMENTS

| | | |
|---|---|---|
| CN | 107384867 A | 11/2017 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |
| JP | 2013-512694 A | 4/2013 |
| WO | 2007103901 A2 | 9/2007 |
| WO | WO 2013/057500 A1 | 4/2013 |
| WO | WO 2013/088147 A1 | 6/2013 |
| WO | WO 2013/173835 A1 | 11/2013 |
| WO | WO 2013/188427 A1 | 12/2013 |
| WO | 2015157636 A1 | 10/2015 |
| WO | 2015189356 A1 | 12/2015 |
| WO | WO 2015/189357 A1 | 12/2015 |
| WO | WO 2016/053338 A1 | 4/2016 |
| WO | WO 2016/096903 A1 | 6/2016 |
| WO | WO2016/174085 A1 | 11/2016 |
| WO | 2017048614 A1 | 3/2017 |
| WO | 2018005712 A1 | 1/2018 |
| WO | WO 2018/081473 A1 | 5/2018 |
| WO | 2018102761 A1 | 6/2018 |
| WO | 2018170188 A2 | 9/2018 |

OTHER PUBLICATIONS

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley, et al., "Cancer Regression and Autoimmunity in Patients After Clonal Repopulation with Antitumor Lymphocytes", Science, Oct. 2002, 298, 850-54.

International Search Report and Written Opinion for International Patent Application No. PCT/US2018/012633 dated May 25, 2018, 11 pages.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. "Adoptive cell therapy for the treatment of patients with metastatic melanoma", Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Somerville RP, et al., "Clinical scale rapid expansion of lymphocytes for adoptive cell transfer therapy in the WAVE® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Ye et al. ; Engineered artificial antigen presenting cells facilitate direct and efficient expansion of tumor infiltrating ymphocytes; Journal of Translational Medicine 2011, 9:131, 1-13.

Search Report and Written Opinion for Singapore Patent Application No. 11201904354P, 10 pages.

International Search Report dated Feb. 27, 2018 for International Patent Application No. PCT/US2017/062219, 6 pages.

M. J. Besser et al, "Clinical Responses in a Phase II Study Using Adoptive Transfer of Short-term Cultured Tumor nfiltration Lymphocytes in Metastatic Melanoma Patients", Clinical Cancer Research, vol. 16, No. 9, Apr. 20, 2010 (Apr. 20, 2010), p. 2646-2655.

Dudley Mark E et al, "Adoptive cell transfer therapy following non-myeloablative but lymphodepleting chemotherapy for the treatment of patients with refractory metastatic melanoma", Journal of Clinical Oncology, American Society of Clinical Oncology, US, vol. 23, No. 10, Apr. 1, 2005 (Apr. 1, 2005), p. 2346-2357.

Dudley M E et al, "Generation of tumor-infiltrating lymphocyte cultures for use in adoptive transfer therapy for melanoma patients", Journal of Immunotherapy,, vol. 26, No. 4, Jul. 1, 2003 (Jul. 1, 2003), p. 332-342.

Rosenberg S A et al, "Treatment of Patients With Metastatic Melanoma With Autologous Tumor-Infiltrating Lymphocytes and Interleukin 2", Journal of the National Cancer Institute, Oxford University Press, GB, vol. 86, No. 15, Aug. 3, 1994 (Aug. 3, 1994), p. 1159-1166.

Glen M. Chew et al, "TIGIT Marks Exhausted T Cells, Correlates with Disease Progression, and Serves as a Target for Immune Restoration in HIV and SIV Infection", PLOS Pathogens, vol. 12, No. 1, Jan. 7, 2016 (Jan. 7, 2016), p. e1005349.

Simpson-Abelson M R et al, "Emigrant pre-REP tumor infiltrating lymphocytes profoundly differ from remnant T-cells", Cancer Research Jul. 1, 2017 American Association for Cancer Research Inc. NLD, vol. 77, No. 13, Supplement 1, Jul. 1, 2017 (Jul. 1, 2017).

Written Opinion for International Patent Application No. PCT/US2017/062219, 9 pages.

Translation of Office Action dated Aug. 3, 2021 for Japanese Patent Application No. 2019-525747, 7 pages.

(56) References Cited

OTHER PUBLICATIONS

Beane JD et al., Clinical scale zinc finger nuclease-mediated gene editing of PD-1 in tumor infiltrating lymphocytes for the treatment of metastatic melanoma., Molecular Therapy, 2015, 23, 8, 1380-1390.
Junko Matsuzaki, Basis and Clinical Application of LAG-3 molecule, The Medical Frontline, 2015, 70, 3, 360-365.
Kawakami Y. et al., Interleukin 4 promotes the growth of tumor-infiltrating lymphocytes cytotoxic for human autologous melanoma., The Journal of Experimantal Medicine, 1988, 168, 2183-2191.

* cited by examiner

SEQUENCE LISTING

```
<160> NUMBER OF SEQ ID NOS: 8

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

```
                    50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                     85                  90                  95

Ala Arg Tyr Tyr Asp Asp His Tyr Cys Leu Asp Tyr Trp Gly Gln Gly
                100                 105                 110

Thr Thr Leu Thr Val Ser Ser Ala Lys Thr Thr Ala Pro Ser Val Tyr
                115                 120                 125

Pro Leu Ala Pro Val Cys Gly Gly Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
                180                 185                 190

Thr Trp Pro Ser Gln Ser Ile Thr Cys Asn Val Ala His Pro Ala Ser
                195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 2
```

```
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
```

```
            100                 105                 110

Ala Thr Ile Val Glu Phe Leu Asn Arg Trp Ile Thr Phe Cys Gln Ser
        115                 120                 125

Ile Ile Ser Thr Leu Thr
        130

<210> SEQ ID NO 4
<211> LENGTH: 132
<212> TYPE: PRT
<213> ORGANISM: Artificial Sequence
<220> FEATURE:
<223> OTHER INFORMATION: aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4

<400> SEQUENCE: 5

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125
```

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7

<400> SEQUENCE: 6

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15

<400> SEQUENCE: 7

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 8

```
<211> LENGTH: 132
<212> TYPE: PRT
<213> ORGANISM: Artificial Sequence
<220> FEATURE:
<223> OTHER INFORMATION: IL-21

<400> SEQUENCE: 8

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130
```

REMNANT TUMOR INFILTRATING LYMPHOCYTES AND METHODS OF PREPARING AND USING THE SAME

CROSS-REFERENCE TO RELATED APPLICATIONS

This application is a continuation of U.S. patent application Ser. No. 16/462,056, which is a U.S. National Stage of International Application No. PCT/US2017/062219, filed Nov. 17, 2017, which claims the benefit of priority to U.S. Provisional Application No. 62/423,750, filed Nov. 17, 2016, and U.S. Provisional Application No. 62/460,441, filed Feb. 17, 2017, the entireties of which are incorporated herein by reference.

FIELD OF THE INVENTION

Methods and compositions for expansion of tumor infiltrating lymphocytes from tumor remnants are disclosed in some embodiments.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. Adoptive T cell therapy with autologous TILs provides up to 55% objective response rates and durable regression in >25% of patients with metastatic melanoma. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. Processes for generating TILs from resected tumors include the step of morcellating the tumor into 1-3 mm$^3$ fragments, and expanding TILs in the presence of interleukin 2 (IL-2) in the pre-rapid expansion protocol (pre-REP or initiation) step. During the pre-REP step, tumor-resident immune cells emigrate and proliferate, and these TILs are subjected to a second REP process, with irradiated peripheral blood mononuclear cell (PBMC) feeders, anti-CD3 antibody (OKT-3, muromonab), and IL-2, which greatly increases their numbers. To date, all TIL expansion processes discard residual tumor fragments following the pre-REP process.

Direct enzymatic digestion of resected tumors has been previously explored as an alternative to pre-REP, but has been reported to yield less TIL cultures, resulting in a decreased ability to obtain TILs than from pre-REP initiation processes with IL-2. Dudley, et al., *J. Immunother.* 2003, 26, 332-42. For this reason, digestion has not been further explored in the development of TILs as a therapy for cancer.

TILs obtained from the pre-REP and REP processes have dominated the clinical studies of TILs to date, which have offered modest clinical responses, and the field remains challenging, particularly in the extension of TIL therapy from melanoma to other tumor types. Goff, et al., *J. Clin. Oncol.* 2016, 34, 2389-97; Dudley, et al., *J. Clin. Oncol.* 2008, 26, 5233-39; Rosenberg, et al., *Clin. Cancer Res.* 2011, 17, 4550-57. Much focus has been placed on selection of TILs during expansion to either select particular subsets (such as CD8$^+$ T cells) or to target driver mutations such as a mutated ERBB2IP epitope or driver mutations in the KRAS oncogene. Tran, et al., *N. Engl. J. Med.* 2016, 375, 2255-62; Tran, et al., *Science* 2014, 344, 641-45. However, such selection approaches, even if they can be developed to show efficacy in larger clinical trials, add significantly to the duration, complexity, and cost of performing TIL therapy and limit the potential for widespread use of TIL therapy in different types of cancers. Thus, there is an urgent need to develop processes capable of providing TILs with improved properties for use in cancer therapies.

The invention provides the unexpected finding that TILs with improved properties may be obtained from processes based on tumor remnant cells, and that such remnant TILs (rTILs) are phenotypically and functionally distinct from normal emigrant TILs (eTILs). The use of rTILs and combinations of rTILs and eTILs in cancer immunotherapy provides significant advantages over prior eTIL-based therapies.

SUMMARY OF THE INVENTION

In an embodiment, the invention includes a method for preparing remnant tumor infiltrating lymphocytes (rTILs) for adoptive T cell therapy, the method comprising:
    (a) obtaining tumor tissue from the patient, wherein the tumor tissue comprises tumor infiltrating lymphocytes (TILs);
    (b) fragmenting the tumor tissue;
    (c) treating the tumor tissue in a gas permeable container with a first cell culture medium and interleukin 2 (IL-2) to provide tumor remnants and emergent TILs (eTILs);
    (d) removing at least a plurality of the eTILs;
    (e) enzymatically digesting the tumor remnants into tumor remnant cells using a digest mixture; and
    (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
    wherein the rTILs express reduced levels of a T cell exhaustion marker relative to the eTILs, and wherein the T cell exhaustion marker is selected from the group consisting of TIM3, LAG3, TIGIT, PD-1, CTLA-4, and combinations thereof.

In an embodiment, the invention includes a method for preparing remnant tumor infiltrating lymphocytes (rTILs) for adoptive T cell therapy, the method comprising:
    (a) obtaining tumor tissue from the patient, wherein the tumor tissue comprises tumor infiltrating lymphocytes (TILs);
    (b) fragmenting the tumor tissue;
    (c) treating the tumor tissue in a gas permeable container with a first cell culture medium and interleukin 2 (IL-2) to provide tumor remnants and emergent TILs (eTILs);
    (d) removing at least a plurality of the eTILs;
    (e) enzymatically digesting the tumor remnants into tumor remnant cells using a digest mixture; and
    (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
    wherein the rTILs express reduced levels of a T cell exhaustion marker relative to the eTILs, wherein the T cell exhaustion marker is selected from the group consisting of TIM3, LAG3, TIGIT, PD-1, CTLA-4, and combinations thereof, and wherein the tumor tissue is selected from the group consisting of melanoma tumor tissue, head and neck tumor tissue, breast tumor tissue, renal tumor tissue, pancreatic tumor tissue, glioblastoma tumor tissue, lung tumor tissue, colorectal tumor tissue, sarcoma tumor tissue, triple negative breast tumor tissue, cervical tumor tissue, ovarian tumor tissue, and acute myeloid leukemia bone marrow or tumor tissue.

In an embodiment, the invention includes a method for preparing remnant tumor infiltrating lymphocytes (rTILs) for adoptive T cell therapy, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture; and (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, CTLA-4, and combinations thereof, and wherein the irradiated feeder cells comprise irradiated allogeneic peripheral blood mononuclear cells.

In an embodiment, the invention includes a method for preparing remnant tumor infiltrating lymphocytes (rTILs) for adoptive T cell therapy, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture; and (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein IL-2 is present in the second cell culture medium at an initial concentration of about 3000 IU/mL and OKT-3 antibody is present in the second cell culture medium at an initial concentration of about 30 ng/mL.

In an embodiment, the invention includes a method for preparing remnant tumor infiltrating lymphocytes (rTILs) for adoptive T cell therapy, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture; and (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein at least one T cell exhaustion marker in $CD8^+$ and $CD4^+$ T cells in the rTILs is reduced by at least 10% relative to the eTILs.

In an embodiment, the invention includes a method for preparing remnant tumor infiltrating lymphocytes (rTILs) for adoptive T cell therapy, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture; and (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein the T cell exhaustion marker is a LAG3 marker in $CD8^+$ T cells, and wherein the LAG3 marker in the rTILs is reduced by at least 2-fold relative to the eTILs.

In an embodiment, the invention includes a method for preparing remnant tumor infiltrating lymphocytes (rTILs) for adoptive T cell therapy, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture; and (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the T cell exhaustion marker is a TIM3 marker in CD8$^+$ T cells, and wherein the LAG3 marker in the rTILs is reduced by at least 3-fold relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the T cell exhaustion marker is a TIM3 marker in CD4$^+$ T cells, and wherein the LAG3 marker in the rTILs is reduced by at least 2-fold relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the TIM3 marker and the LAG3 marker in the rTILs are undetectable by flow cytometry.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein CD56$^+$ expression in the rTILs is reduced by at least 3-fold relative to CD56$^+$ expression in the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein CD69$^+$ expression in the rTILs is increased by at least 2-fold relative to CD69$^+$ expression in the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and wherein the digest mixture comprises deoxyribonuclease, collagenase, and hyaluronidase.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the first cell culture medium further comprises a cytokine selected from the group consisting of IL-4, IL-7, IL-15, IL-21, and combinations thereof.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof.

In an embodiment, the invention includes a method of treating a cancer in a patient in need of such treatment, wherein the treatment comprises delivering a therapeutically effective amount of rTILs to a patient, wherein the rTILs are prepared according a method comprising the steps of:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof.

In an embodiment, the invention includes a method treating a cancer in a patient in need of such treatment, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture;
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof,
  (g) treating the patient with a non-myeloablative lymphodepletion regimen prior to administering the rTILs to the patient;
  (h) administering a therapeutically effective amount of rTILs to the patient; and
  (i) treating the patient with a high-dose IL-2 regimen starting on the day after administration of the rTILs to the patient.

In an embodiment, the invention includes a method treating a cancer in a patient in need of such treatment, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture;
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient,
wherein the cancer is selected from the group consisting of melanoma, double-refractory melanoma, ovarian cancer, cervical cancer, lung cancer, bladder cancer, breast cancer, head and neck cancer, renal cell carcinoma, acute myeloid leukemia, colorectal cancer, sarcoma, non-small cell lung cancer (NSCLC), and triple negative breast cancer.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and (i) treating the patient with a high-dose IL-2 regimen starting on the day after administration of the rTILs to the patient,
wherein the high-dose IL-2 regimen comprises 600,000 or 720,000 IU/kg of aldesleukin, or a biosimilar or variant thereof, administered as a 15-minute bolus intravenous infusion every eight hours until tolerance.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs, and wherein the T cell exhaustion marker is selected from the group consisting of TIM3, LAG3, TIGIT, PD-1, CTLA-4, and combinations thereof.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, CTLA-4, and combinations thereof, and
wherein the tumor tissue is selected from the group consisting of melanoma tumor tissue, head and neck tumor tissue, breast tumor tissue, renal tumor tissue, pancreatic tumor tissue, glioblastoma tumor tissue, lung tumor tissue, colorectal tumor tissue, sarcoma tumor tissue, triple negative breast tumor tissue, cervical tumor tissue, ovarian tumor tissue, and acute myeloid leukemia bone marrow or tumor tissue.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, CTLA-4, and combinations thereof, and
wherein the irradiated feeder cells comprise irradiated allogeneic peripheral blood mononuclear cells.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein IL-2 is present in the second cell culture medium at an initial concentration of about 3000 IU/mL and OKT-3 antibody is present in the second cell culture medium at an initial concentration of about 30 ng/mL.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein at least one T cell exhaustion marker in CD8$^+$ and CD4$^+$ T cells in the rTILs is reduced by at least 10% relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the T cell exhaustion marker is a LAG3 marker in CD8$^+$ T cells, and wherein the LAG3 marker in the rTILs is reduced by at least 2-fold relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the T cell exhaustion marker is a TIM3 marker in CD8$^+$ T cells, and wherein the LAG3 marker in the rTILs is reduced by at least 3-fold relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the T cell exhaustion marker is a TIM3 marker in CD4$^+$ T cells, and wherein the LAG3 marker in the rTILs is reduced by at least 2-fold relative to the eTILs.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the TIM3 marker and the LAG3 marker in the rTILs are undetectable by flow cytometry.

In an embodiment, the invention includes a method for preparing remnant tumor infiltrating lymphocytes (rTILs) for adoptive T cell therapy, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture; and
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and wherein CD56⁺ expression in the rTILs is reduced by at least 3-fold relative to CD56⁺ expression in the eTILs.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein CD69⁺ expression in the rTILs is increased by at least 2-fold relative to CD69⁺ expression in the eTILs.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the digest mixture comprises deoxyribonuclease, collagenase, and hyaluronidase.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the first cell culture medium further comprises a cytokine selected from the group consisting of IL-4, IL-7, IL-15, IL-21, and combinations thereof.

In an embodiment, the invention includes a method for preparing remnant tumor infiltrating lymphocytes (rTILs) for adoptive T cell therapy, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof.

In an embodiment, the invention includes a method of treating a cancer in a patient in need of such treatment, wherein the treatment comprises delivering a therapeutically effective amount of rTILs to a patient, wherein the rTILs are prepared according a method comprising the steps of:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient; and
(i) treating the patient with a high-dose IL-2 regimen starting on the day after administration of the rTILs to the patient.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient,
wherein the cancer is selected from the group consisting of melanoma, double-refractory melanoma, ovarian cancer, cervical cancer, lung cancer, bladder cancer, breast cancer, head and neck cancer, renal cell carcinoma, acute myeloid leukemia, colorectal cancer, sarcoma, non-small cell lung cancer (NSCLC), and triple negative breast cancer.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein the second cell culture medium further comprises a cytokine selected from the group consisting of IL-4, IL-7, IL-15, IL-21, and combinations thereof, (g) treating the patient with a non-myeloablative lymphodepletion regimen prior to administering the rTILs to the patient, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days;

(h) administering a therapeutically effective amount of rTILs to the patient, wherein a therapeutically effective amount of eTILs are simultaneously administered to the patient in a mixture with the rTILs; and (i) treating the patient with a high-dose IL-2 regimen starting on the day after administration of the rTILs to the patient.

In an embodiment, the invention includes a method treating a cancer in a patient in need of such treatment, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing the eTILs;

(e) enzymatically digesting the tumor remnants into tumor remnant cells using a digest mixture;

(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein the second cell culture medium further comprises a cytokine selected from the group consisting of IL-4, IL-7, IL-15, IL-21, and combinations thereof, (g) treating the patient with a non-myeloablative lymphodepletion regimen prior to administering the rTILs to the patient;

(h) administering a therapeutically effective amount of rTILs to the patient, wherein a therapeutically effective amount of eTILs are simultaneously administered to the patient in a mixture with the rTILs; and (i) treating the patient with a high-dose IL-2 regimen starting on the day after administration of the rTILs to the patient, wherein the high-dose IL-2 regimen comprises 600,000 or 720,000 IU/kg of aldesleukin, or a biosimilar or variant thereof, administered as a 15-minute bolus intravenous infusion every eight hours until tolerance.

In an embodiment, the invention includes a process for generating an expanded number of tumor remnant cells that include tumor infiltrating lymphocytes (TILs) from a patient for adoptive T cell therapy. In some embodiments, the process of the invention may include the step of obtaining tumor tissue from the patient, wherein the tumor tissue comprises TILs. In some embodiments, the process of the invention may include the step of fragmenting the tumor tissue. In some embodiments, the process of the invention may include the step of treating the tumor tissue in a gas permeable container with cell culture media and interleukin 2 (IL-2) and other T cell growth factors or agonistic antibodies to provide tumor remnants and an expanded number of TILs. In some embodiments, the process of the invention may include the step of removing the expanded number of TILs. In some embodiments, the process of the invention may include the step of enzymatically digesting the tumor remnants into tumor remnant cells. In some embodiments, the process of the invention may include the step of treating the tumor remnant cells with cell culture media, irradiated feeder cells, anti-CD3 monoclonal antibody (muromonab or OKT-3), and IL-2 to provide the expanded number of tumor remnant cells. In some embodiments, the tumor remnant cells prepared according to the processes of the invention may include TILs that express reduced levels of at least one marker selected from the group consisting of TIM3, LAG3, PD-1, and combinations thereof. In some embodiments, the tumor tissue may be selected from the group consisting of melanoma tumor tissue, head and neck tumor tissue, breast tumor tissue, renal tumor tissue, pancreatic tumor tissue, lung tumor tissue, and colorectal tumor tissue.

In an embodiment, the invention may include method of treating a tumor in a patient in need of such treatment. In some embodiments, the treatment may include delivering a therapeutically effective amount of an expanded number of tumor remnant cells to the patient, wherein the expanded number of tumor remnant cells may be prepared according to any process described herein.

BRIEF DESCRIPTION OF THE DRAWINGS

The foregoing summary, as well as the following detailed description of the invention, will be better understood when read in conjunction with the appended drawings.

BRIEF DESCRIPTION OF THE SEQUENCE LISTING

Figure 1:
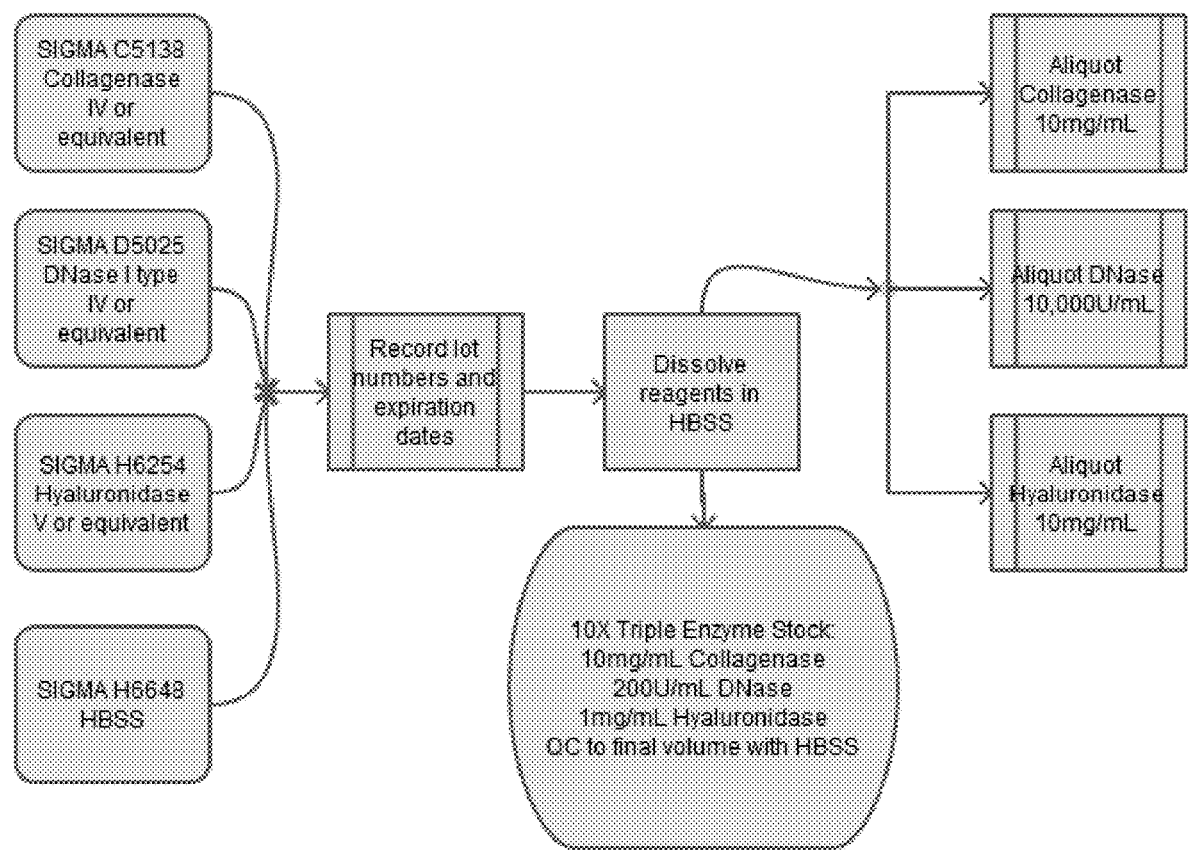
FIG. 1 illustrates an exemplary diagram of the tumor digestion solution preparation.

SEQ ID NO:1 is the amino acid sequence of the heavy chain of muromonab.
SEQ ID NO:2 is the amino acid sequence of the light chain of muromonab.
SEQ ID NO:3 is the amino acid sequence of a recombinant human IL-2 protein.
SEQ ID NO:4 is the amino acid sequence of aldesleukin.
SEQ ID NO:5 is the amino acid sequence of a recombinant human IL-4 protein.
SEQ ID NO:6 is the amino acid sequence of a recombinant human IL-7 protein.
SEQ ID NO:7 is the amino acid sequence of a recombinant human IL-15 protein.
SEQ ID NO:8 is the amino acid sequence of a recombinant human IL-21 protein.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "exhausted phenotype" and "exhaustion marker" refer to cell surface markers characteristic of T cell exhaustion in response to chronic T cell receptor (TCR) stimulation by antigen. T cells exhibiting an exhausted phenotype express inhibitory receptors, such as T cell immunoglobulin and mucin-domain containing-3 (TIM3 or TIM-3), lymphocyte-activation gene 3 (LAG3 or LAG-3), T cell immunoreceptor with immunoglobulin and ITIM domains (TIGIT), and programmed cell death protein 1 (PD-1), and lack effector cytokine production and the ability to mount an effective immune response. Exhaustion in T cells is described in Yi, et al., Immunology 2010, 129, 474-81, the disclosure of which is incorporated by reference herein.

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "antigen" refers to a substance that induces an immune response. In some embodiments, an antigen is a molecule capable of being bound by an antibody or a TCR if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried. A therapeutically effective amount may be "an anti-tumor effective amount" and/or a "tumor-inhibiting effective amount," which may be the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the cytotoxic lymphocytes or rTILs described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Cytotoxic lymphocyte or rTIL compositions may also be administered multiple times at these dosages. The cytotoxic lymphocytes or rTILs can be administered by using infusion techniques that are commonly known in immunotherapy (see, e.g., Rosenberg et al., *N. Eng. J. Med.* 319: 1676, 1988). The optimal dosage and treatment regime for a particular patient can readily be determined by one skilled in the art of medicine by monitoring the patient for signs of disease and adjusting the treatment accordingly.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined herein.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). In certain embodiments, the term "Primary TILs" may include rTILs and mixtures of eTILs and rTILs.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$ to $1.5 \times 10^{10}$ cells for infusion.

The terms "peripheral blood mononuclear cells" and "PBMCs" refers to a peripheral blood cell having a round nucleus, including lymphocytes (such as T cells, B cells, and NK cells) and monocytes. Preferably, the peripheral blood mononuclear cells are irradiated allogeneic peripheral blood mononuclear cells. PBMCs are a type of antigen-presenting cell.

By "cryopreserved TILs" herein is meant that TILs, either primary, bulk, or expanded (REP TILs), are treated and stored in the range of about −150° C. to −60° C. General methods for cryopreservation are also described elsewhere herein. For clarity, "cryopreserved TILs" are distinguishable from frozen tissue samples which may be used as a source of primary TILs including rTILs.

By "thawed cryopreserved TILs" herein is meant a population of TILs (such as rTILs) that was previously cryopreserved and then treated to return to room temperature or higher, including but not limited to cell culture temperatures or temperatures wherein TILs may be administered to a patient.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

The term "conservative amino acid substitutions" means amino acid sequence modifications which do not abrogate the binding of the antibody to the antigen. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in a protein is preferably replaced with another amino acid residue from the same class. Methods of identifying amino acid conservative substitutions which do not eliminate antigen binding are well-known in the art (see, e.g., Brummell, et al., *Biochemistry* 1993, 32, 1180-1187; Kobayashi, et al., Protein Eng. 1999, 12, 879-884 (1999); and Burks, et al., *Proc. Natl. Acad. Sci. USA* 1997, 94, 412-417).

"Pegylation" refers to a modified antibody or fusion protein, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The protein or antibody to be pegylated may be an aglycosylated protein or antibody. Methods for pegylation are known in the art and can be applied to the antibodies of the invention, as described for example in European Patent Nos. EP 0154316 and EP 0401384 and U.S. Pat. No. 5,824,778, the disclosures of each of which are incorporated by reference herein.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706. Anti-CD3 antibodies also include the UHCT1 clone (commercially available from BioLegend, San Diego, Calif., USA), also known as T3 and CD3ε.

TABLE 1

Amino acid sequences of muromonab.

| Identifier | Sequence (One-Letter Amino Acid Symbols) | | | | | |
|---|---|---|---|---|---|---|
| SEQ ID NO: 1 Muromonab heavy chain | QVQLQQSGAE | LARPGASVKM | SCKASGYTFT | RYTMHWVKQR | PGQGLEWIGY | INPSRGYTNY | 60 |
| | NQKFKDKATL | TTDKSSSTAY | MQLSSLTSED | SAVYYCARYY | DDHYCLDYWG | QGTTLTVSSA | 120 |
| | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 Muromonab light chain | QIVLTQSPAI | MSASPGEKVT | MTCSASSSVS | YMNWYQQKSG | TSPKRWIYDT | SKLASGVPAH | 60 |
| | FRGSGSGTSY | SLTISGMEAE | DAATYYCQQW | SSNPFTFGSG | TKLEINRADT | APTVSIFPPS | 120 |
| | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IIL-7 receptor alpha and common gamma chain receptor, which in a series of signals important for T cell development within the thymus and survival within the periphery. Recombinant human IL-4 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-7 recombinant protein, Cat. No. Gibco PHC0071). The amino acid sequence of recombinant human IL-7 suitable for use in the invention is given in Table 2 (SEQ ID NO:6).

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTEK TQLQLEHLLL DLQMILNGIN NYKNPKLTRM LTFKFYMPKK ATELKHLQCL EEELKPLEEV LNLAQSKNFH LRPRDLISNI NVIVLELKGS ETTFMCEYAD ETATIVEFLN RWITFCQSII STLT | 60 120 134 |
| SEQ ID NO: 4 Aldesleukin | PTSSSTKKTQ LQLEHLLLDL QMILNGINNY KNPKLTRMLT FKFYMPKKAT ELKHLQCLEE ELKPLEEVLN LAQSKNFHLR PRDLISNINV IVLELEGSET TFMCEYADET ATIVEFLNRW ITFSQSIIST LT | 60 120 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH EKDTRCLGAT AQQFHRHKQL IRFLKRLDRN LWGLAGLNSC PVKEANQSTL ENFLERLKTI MREKYSKCSS | 60 120 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA ARKLRQFLKM NSTGDFDLHL LKVSEGTTIL LNCTGQVKGR KPAALGEAQP TKSLEENKSL KEQKKLNDLC FLKRLLQEIK TCWNKILMGT KEH | 60 120 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI HDTVENLIIL ANNSLSSNGN VTESGCKECE ELEEKNIKEF LQSFVHIVQM FINTS | 60 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS | 60 120 132 |

The term "IL-4" (also referred to herein as "IL4") refers to the cytokine known as interleukin 4, which is produced by Th2 T cells and by eosinophils, basophils, and mast cells. IL-4 regulates the differentiation of naive helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MEW expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-4 recombinant protein, Cat. No. Gibco CTP0043).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4$^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:8).

The term "biosimilar" means a biological product, including a monoclonal antibody or fusion protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody, antibody fragment, or protein. Pegylation may, for example, increase the biological (e.g., serum) half life of the antibody or protein. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody or protein to be pegylated may be an aglycosylated antibody. Methods for pegylation are known in the art and can be applied to the antibodies of the invention, as described for example in European Patent Nos. EP 0154316 and EP 0401384.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T cells, tumor clearance by the immune system is rare because of immune suppression by the microenvironment.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the invention can, in alternate embodiments, be more specifically defined by any of the transitional terms "comprising," "consisting essentially of," and "consisting of."

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Methods of Expanding Remnant Tumor Infiltrating Lymphocytes

In an embodiment, the invention includes a method of expanding remnant tumor infiltrating lymphocytes (rTILs) after digestion of a tumor as described herein.

In an embodiment, the invention includes a method of expanding rTILs, the method comprising contacting a population of rTILs comprising at least one rTIL with IL-2, thereby expanding rTILs.

In an embodiment, the invention provides a method of expanding a population of rTILs, the method comprising the steps as described in Jin, et al., *J. Immunotherapy* 2012, 35, 283-292, the disclosure of which is incorporated by reference herein. For example, the tumor may be placed in enzyme media and mechanically fragmented for approximately 1 minute. The mixture may then be incubated for 30 minutes at 37° C. in 5% $CO_2$ and then mechanically fragmented again for approximately 1 minute. After incubation for 30 minutes at 37° C. in 5% $CO_2$, the tumor may be mechanically fragmented a third time for approximately 1 minute. If after the third mechanical disruption, large pieces of tissue are present, 1 or 2 additional mechanical dissociations may be applied to the sample, with or without 30 additional minutes of incubation at 37° C. in 5% $CO_2$. At the end of the final incubation, if the cell suspension contains a large number of red blood cells or dead cells, a density gradient separation using Ficoll may be performed to remove these cells. TIL cultures were initiated in 24-well plates (Costar 24-well cell culture cluster, flat bottom; Corning Incorporated, Corning, N.Y.), each well may be seeded with $1 \times 10^6$ tumor digest cells or one tumor fragment approximately 1-8 $mm^3$ in size in 2 mL of complete medium (CM) with IL-2 (6000 IU/mL; Chiron Corp., Emeryville, Calif.). CM consists of RPMI 1640 with GlutaMAX, supplemented with 10% human AB serum, 25 mM Hepes, and 10 mg/mL gentamicin. Cultures may be initiated in gas-permeable flasks with a 40 mL capacity and a 10 $cm^2$ gas-permeable silicon bottom (G-Rex 10; Wilson Wolf Manufacturing, New Brighton), each flask may be loaded with $10\text{-}40 \times 10^6$ viable tumor digest cells or 5-30 tumor fragments in 10-40 mL of CM with IL-2. G-Rex 10 and 24-well plates may be incubated in a humidified incubator at 37° C. in 5% $CO_2$ and 5 days after culture initiation, half the media may be removed and replaced with fresh CM and IL-2 and after day 5, half the media may be changed every 2-3 days. A rapid expansion protocol (REP) for TILs may be performed using T-175 flasks and gas-permeable bags or gas-permeable G-Rex flasks, as described elsewhere herein. For REP in T-175 flasks, $1 \times 10^6$ rTILs may be suspended in 150 mL of media in each flask. The rTIL may be cultured in a 1 to 1 mixture of CM and AIM-V medium (50/50 medium), supplemented with 3000 IU/mL of IL-2 and 30 ng/mL of anti-CD3 antibody (OKT-3). The T-175 flasks may be incubated at 37° C. in 5% $CO_2$. Half the media may be changed on day 5 using 50/50 medium with 3000 IU/mL of IL-2. On day 7, cells from 2 T-175 flasks may be combined in a 3 L bag and 300 mL of AIM-V with 5% human AB serum and 3000 IU/mL of IL-2 may be added to the 300 mL of TIL suspension. The number of cells in each bag may be counted every day or two days, and fresh media may be added to keep the cell count between 0.5 and $2.0 \times 10^6$ cells/mL. For REP in 500 mL capacity flasks with 100 $cm^2$ gas-permeable silicon bottoms (e.g., G-Rex 100, Wilson Wolf Manufacturing, as described elsewhere herein), $5 \times 10^6$ or $10 \times 10^6$ TILs may be cultured in 400 mL of 50/50 medium, supplemented with 3000 IU/mL of IL-2 and 30 ng/mL of anti-CD3 antibody (OKT-3). The G-Rex100 flasks may be incubated at 37° C. in 5% $CO_2$. On day five, 250 mL of supernatant may be removed and placed into centrifuge bottles and centrifuged at 1500 rpm (491 g) for 10 minutes. The obtained TIL pellets may be resuspended with 150 mL of fresh 50/50 medium with 3000 IU/mL of IL-2 and added back to the G-Rex 100 flasks. When TIL are expanded serially in G-Rex 100 flasks, on day seven the TIL in each G-Rex100 are suspended in the 300 mL of media present in each flask and the cell suspension may be divided into three 100 mL aliquots that may be used to seed 3 G-Rex100 flasks. About 150 mL of AIM-V with 5% human AB serum and 3000 IU/mL of IL-2 may then be added to each flask. G-Rex100 flasks may then be incubated at 37° C. in 5% $CO_2$, and after four days, 150 mL of AIM-V with 3000 IU/mL of IL-2 may be added to each G-Rex100 flask. After this, the REP may be completed by harvesting cells on day 14 of culture.

In an embodiment, a method of expanding or treating a cancer includes a step wherein TILs are obtained from a patient tumor sample. A patient tumor sample may be obtained using methods known in the art. For example, TILs may be cultured from enzymatic tumor digests and tumor fragments (about 1 to about 8 $mm^3$ in size) from sharp dissection. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator or fragmenter). Tumor digests may be produced by placing the tumor in enzymatic media and mechanically fragmenting the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In an embodiment, REP of rTILs can be performed in a gas permeable container using any suitable method. For example, rTILs can be rapidly expanded using non-specific T cell receptor stimulation in the presence of interleukin-2 (IL-2), interleukin-15 (IL-15), and/or interleukin-21 (IL-21), as described, e.g., in International Patent Application Publication Nos. WO 2015/189356 A1 and WO 2015/189356 A1, the disclosures of each of which are incorporated by reference herein. The non-specific T cell receptor stimulus can include, for example, about 30 ng/mL of OKT-3, a monoclonal anti-CD3 antibody (commercially available from Ortho-McNeil, Raritan, N.J. or Miltenyi Biotech, Inc., San Diego, Calif., USA). TILs can be rapidly expanded by further stimulation of the TILs in vitro with one or more antigens, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gp100:209-217 (210M), optionally in the presence of a T cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2.

In an embodiment, a method for expanding TILs may include using about 5000 mL to about 25000 mL of cell medium, about 5000 mL to about 10000 mL of cell culture medium, or about 5800 mL to about 8700 mL of cell culture medium. In an embodiment, a method for expanding TILs may include using about 1000 mL to about 2000 mL of cell medium, about 2000 mL to about 3000 mL of cell culture medium, about 3000 mL to about 4000 mL of cell culture medium, about 4000 mL to about 5000 mL of cell culture medium, about 5000 mL to about 6000 mL of cell culture medium, about 6000 mL to about 7000 mL of cell culture medium, about 7000 mL to about 8000 mL of cell culture medium, about 8000 mL to about 9000 mL of cell culture medium, about 9000 mL to about 10000 mL of cell culture medium, about 10000 mL to about 15000 mL of cell culture medium, about 15000 mL to about 20000 mL of cell culture medium, or about 20000 mL to about 25000 mL of cell culture medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad Calif.). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the rapid expansion is performed using a gas permeable container. Such embodiments allow for cell populations to expand from about $5 \times 10^5$ cells/cm$^2$ to between $10 \times 10^6$ and $30 \times 10^6$ cells/cm$^2$. In an embodiment, this expansion occurs without feeding. In an embodiment, this expansion occurs without feeding so long as medium resides at a height of about 10 cm in a gas-permeable flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739 A1, International Patent Application Publication No. WO 2014/210036 A1, U.S. Patent Application Publication No. US 2013/0115617 A1, International Publication No. WO 2013/188427 A1, U.S. Patent Application Publication No. US 2011/0136228 A1, U.S. Pat. No. 8,809,050, International Patent Application Publication No. WO 2011/072088 A2, U.S. Patent Application Publication No. US 2016/0208216 A1, U.S. Patent Application Publication No. US 2012/0244133 A1, International Patent Application Publication No. WO 2012/129201 A1, U.S. Patent Application Publication No. US 2013/0102075 A1, U.S. Pat. No. 8,956,860, International Patent Application Publication No. WO 2013/173835 A1, and U.S. Patent Application Publication No. US 2015/0175966 A1, the disclosures of which are incorporated herein by reference. Such processes are also described in Jin, et al., *J. Immunotherapy* 2012, 35, 283-292, the disclosure of which is incorporated by reference herein.

In an embodiment, the gas permeable container is a G-Rex 10 flask (Wilson Wolf Manufacturing Corporation, New Brighton, Minn., USA). In an embodiment, the gas permeable container includes a 10 cm$^2$ gas permeable culture surface. In an embodiment, the gas permeable container includes a 40 mL cell culture medium capacity. In an embodiment, the gas permeable container provides 100 to 300 million TILs after 2 medium exchanges.

In an embodiment, the gas permeable container is a G-Rex 100 flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 450 mL cell culture medium capacity. In an embodiment, the gas permeable container provides 1 to 3 billion TILs after 2 medium exchanges.

In an embodiment, the gas permeable container is a G-Rex 100M flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 1000 mL cell culture medium capacity. In an embodiment, the gas permeable container provides 1 to 3 billion TILs without medium exchange.

In an embodiment, the gas permeable container is a G-Rex 100L flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 2000 mL cell culture medium capacity. In an embodiment, the gas permeable container provides 1 to 3 billion TILs without medium exchange.

In an embodiment, the gas permeable container is a G-Rex 24 well plate (Wilson Wolf Manufacturing Corporation, New Brighton, Minn., USA). In an embodiment, the gas permeable container includes a plate with wells, wherein each well includes a 2 cm$^2$ gas permeable culture surface. In an embodiment, the gas permeable container includes a plate with wells, wherein each well includes a 8 mL cell culture medium capacity. In an embodiment, the gas permeable container provides 20 to 60 million cells per well after 2 medium exchanges.

In an embodiment, the gas permeable container is a G-Rex 6 well plate (Wilson Wolf Manufacturing Corporation, New Brighton, Minn., USA). In an embodiment, the gas permeable container includes a plate with wells, wherein each well includes a 10 cm$^2$ gas permeable culture surface. In an embodiment, the gas permeable container includes a plate with wells, wherein each well includes a 40 mL cell culture medium capacity. In an embodiment, the gas permeable container provides 100 to 300 million cells per well after 2 medium exchanges.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein for a duration of about 14 to about 42 days, e.g., about 28 days.

In an embodiment, the ratio of rTILs to PBMCs in the rapid expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of rTILs to PBMCs in the rapid expansion is between 1 to 50 and 1 to 300. In an embodiment, the ratio of rTILs to PBMCs in the rapid expansion is between 1 to 100 and 1 to 200.

In an embodiment, the ratio of rTILs to PBMCs (rTIL:PBMC) is selected from the group consisting of 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:225, 1:250, 1:275, 1:300, 1:350, 1:400, 1:450, and 1:500. In a preferred embodiment, the ratio of rTILs to PBMCs (rTIL:PBMC) is about 1:90. In a preferred embodiment, the ratio of TILs to PBMCs (rTIL:PBMC) is about 1:95. In a preferred embodiment, the ratio of rTILs to PBMCs (TIL:PBMC) is about 1:100. In a preferred embodiment, the ratio of rTILs to PBMCs (TIL:PBMC) is about 1:105. In a preferred embodiment, the ratio of rTILs to PBMCs (TIL:PBMC) is about 1:110.

In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In a preferred embodiment, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody.

In an embodiment, a rapid expansion process for TILs may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks, commercially available from Wilson Wolf Manufacturing Corporation, New Brighton, Minn., USA). For TIL rapid expansion in T-175 flasks, $1 \times 10^6$ TILs suspended in 150 mL of media may be added to each T-175 flask. The TILs may be cultured in a 1 to 1 mixture of CM and AIM-V medium, supplemented with 3000 IU (injection units) per mL of IL-2 and 30 ng per mL of anti-CD3 antibody (e.g., OKT-3). The T-175 flasks may be incubated at 37° C. in 5% $CO_2$. Half the media may be exchanged on day 5 using 50/50 medium with 3000 IU per mL of IL-2. On day 7 cells from two T-175 flasks may be combined in a 3 liter bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, for TIL rapid expansions in 500 mL capacity gas permeable flasks with 100 cm gas-permeable silicon bottoms (G-Rex 100, commercially available from Wilson Wolf Manufacturing Corporation, New Brighton, Minn., USA), $5 \times 10^6$ or $10 \times 10^6$ TIL may be cultured in 50/50 medium, supplemented with 5% human AB serum, 3000 IU per mL of IL-2 and 30 ng per mL of anti-CD3 (OKT-3). The G-Rex 100 flasks may be incubated at 37° C. in 5% $CO_2$. On day 5, 250 mL of supernatant may be removed and placed into centrifuge bottles and centrifuged at 1500 rpm (revolutions per minute; 491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-Rex 100 flask. The cells may be harvested on day 14 of culture.

In an embodiment, TILs may be prepared as follows. 2 $mm^3$ tumor fragments are cultured in complete media (CM) comprised of AIM-V medium (Invitrogen Life Technologies, Carlsbad, Calif.) supplemented with 2 mM glutamine (Mediatech, Inc. Manassas, Va.), 100 U/mL penicillin (Invitrogen Life Technologies), 100 µg/mL streptomycin (Invitrogen Life Technologies), 5% heat-inactivated human AB serum (Valley Biomedical, Inc. Winchester, Va.) and 600 IU/mL rhIL-2 (Chiron, Emeryville, Calif.). For enzymatic digestion of solid tumors, tumor specimens was diced into RPMI-1640, washed and centrifuged at 800 rpm for 5 minutes at 15-22° C., and resuspended in enzymatic digestion buffer (0.2 mg/mL Collagenase and 30 units/ml of DNase in RPMI-1640) followed by overnight rotation at room temperature. TILs established from fragments may be grown for 3-4 weeks in CM and expanded fresh or cryopreserved in heat-inactivated HAB serum with 10% dimethylsulfoxide (DMSO) and stored at −180° C. until the time of study. Tumor associated lymphocytes (TAL) obtained from ascites collections were seeded at $3 \times 10^6$ cells/well of a 24 well plate in CM. TIL growth was inspected about every other day using a low-power inverted microscope.

In an embodiment, TILs are expanded in gas-permeable containers. Gas-permeable containers have been used to expand TILs using PBMCs using methods, compositions, and devices known in the art, including those described in U.S. Patent Application Publication No. U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, about 10 L, about 11 L, about 12 L, about 13 L, about 14 L, about 15 L, about 16 L, about 17 L, about 18 L, about 19 L, about 20 L, about 25 L, and about 30 L. In an embodiment, the cell expansion system includes a gas permeable cell bag with a volume range selected from the group consisting of between 50 and 150 mL, between 150 and 250 mL, between 250 and 350 mL, between 350 and 450 mL, between 450 and 550 mL, between 550 and 650 mL, between 650 and 750 mL, between 750 and 850 mL, between 850 and 950 mL, and between 950 and 1050 mL. In an embodiment, the cell expansion system includes a gas permeable cell bag with a volume range selected from the group consisting of between 1 L and 2 L, between 2 L and 3 L, between 3 L and 4 L, between 4 L and 5 L, between 5 L and 6 L, between 6 L and 7 L, between 7 L and 8 L, between 8 L and 9 L, between 9 L and 10 L, between 10 L and 11 L, between 11 L and 12 L, between 12 L and 13 L, between 13 L and 14 L, between 14 L and 15 L, between 15 L and 16 L, between 16 L and 17 L, between 17 L and 18 L, between 18 L and 19 L, and between 19 L and 20 L. In an embodiment, the cell expansion system includes a gas permeable cell bag with a volume range selected from the group consisting of between 0.5 L and 5 L, between 5 L and 10 L, between 10 L and 15 L, between 15 L and 20 L, between 20 L and 25 L, and between 25 L and 30 L. In an embodiment, the cell expansion system utilizes a rocking time of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, and about 28 days. In an embodiment, the cell expansion system utilizes a rocking time of between 30 minutes and 1 hour, between 1 hour and 12 hours, between 12 hours and 1 day, between 1 day and 7 days, between 7 days and 14 days, between 14 days and 21 days, and between 21 days and 28 days. In an embodiment, the cell expansion system utilizes a rocking rate of about 2 rocks/minute, about 5 rocks/minute, about 10 rocks/minute, about 20 rocks/minute, about 30 rocks/minute, and about 40 rocks/minute. In an embodiment, the cell expansion system utilizes a rocking rate of between 2 rocks/minute and 5 rocks/minute, 5 rocks/minute and 10 rocks/minute, 10 rocks/minute and 20 rocks/minute, 20 rocks/minute and 30 rocks/minute, and 30 rocks/minute and 40 rocks/minute. In an embodiment, the cell expansion system utilizes a rocking angle of about 2°, about 3°, about 4°, about 5°, about 6°, about 7°, about 8°, about 9°, about 10°, about 11°, and about 12°. In an embodiment, the cell expansion system utilizes a rocking angle of between 2° and 3°, between 3° and 4°, between 4° and 5°, between 5° and 6°, between 6° and 7°, between 7° and 8°, between 8° and 9°, between 9° and 10°, between 10° and 11°, and between 11° and 12°.

In an embodiment, a method of expanding rTILs further comprises a step wherein rTILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Characteristics of rTILs

In an embodiment, the rTILs of the invention exhibit an exhausted T cell phenotype characterized by one or more T cell exhaustion markers. In an embodiment, the rTILs of the invention exhibit an exhausted T cell phenotype characterized by one or more T cell exhaustion markers using flow cytometry analysis. In an embodiment, the T cell exhaustion marker is PD-1. In an embodiment, the T cell exhaustion marker is LAG3. In an embodiment, the T cell exhaustion marker is TIM3.

In an embodiment, PD-1 expression in rTILs is reduced by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, PD-1 expression in rTILs is reduced by at least 2-fold, at least 3-fold, at least 4-fold, at least 5-fold, at least 6-fold, at least 7-fold, at least 8-fold, at least 9-fold, or at least 10-fold relative to the eTILs.

In an embodiment, LAG3 expression in rTILs is reduced by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, LAG3 expression in rTILs is reduced by at least 2-fold, at least 3-fold, at least 4-fold, at least 5-fold, at least 6-fold, at least 7-fold, at least 8-fold, at least 9-fold, or at least 10-fold relative to the eTILs. In an embodiment, LAG3 expression in rTILs is undetectable by flow cytometry.

In an embodiment, TIM3 expression in rTILs is reduced by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, TIM3 expression in rTILs is reduced by at least 2-fold, at least 3-fold, at least 4-fold, at least 5-fold, at least 6-fold, at least 7-fold, at least 8-fold, at least 9-fold, or at least 10-fold relative to the eTILs. In an embodiment, TIM3 expression in rTILs is undetectable by flow cytometry.

In an embodiment, TIGIT expression in rTILs is reduced by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, TIGIT expression in rTILs is reduced by at least 2-fold, at least 3-fold, at least 4-fold, at least 5-fold, at least 6-fold, at least 7-fold, at least 8-fold, at least 9-fold, or at least 10-fold relative to the eTILs. In an embodiment, TIGIT expression in rTILs is undetectable by flow cytometry.

In an embodiment, CTLA-4 expression in rTILs is reduced by at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, CTLA-4 expression in rTILs is reduced by at least 2-fold, at least 3-fold, at least 4-fold, at least 5-fold, at least 6-fold, at least 7-fold, at least 8-fold, at least 9-fold, or at least 10-fold relative to the eTILs. In an embodiment, CTLA-4 expression in rTILs is undetectable by flow cytometry.

In an embodiment, CD69 expression in rTILs is increased by at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, CD69 expression in rTILs is increased by at least 2-fold, at least 3-fold, at least 4-fold, at least 5-fold, at least 6-fold, at least 7-fold, at least 8-fold, at least 9-fold, or at least 10-fold relative to the eTILs.

In an embodiment, S1PR1 (sphingosine-1-phosphate receptor 1) expression in rTILs is decreased by at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, S1PR1 expression in rTILs is decreased by at least 2-fold, at least 3-fold, at least 4-fold, at least 5-fold, at least 6-fold, at least 7-fold, at least 8-fold, at least 9-fold, or at least 10-fold relative to the eTILs.

In an embodiment, telomere length in rTILs is increased by at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, telomere length in rTILs is increased by at least 2-fold, at least 3-fold, at least 4-fold, at least 5-fold, at least 6-fold, at least 7-fold, at least 8-fold, at least 9-fold, or at least 10-fold relative to the eTILs.

In an embodiment, CD28 expression in rTILs is increased by at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, CD28 expression in rTILs is increased by at least 2-fold, at least 3-fold, at least 4-fold, at least 5-fold, at least 6-fold, at least 7-fold, at least 8-fold, at least 9-fold, or at least 10-fold relative to the eTILs.

In an embodiment, CD27 expression in rTILs is increased by at least 10%, at least 20%, at least 30%, at least 40%, at least 50%, at least 60%, at least 70%, at least 80%, at least 90%, at least 100%, at least 110%, at least 120%, at least 130%, at least 140%, or at least 150% relative to the eTILs. In an embodiment, CD27 expression in rTILs is increased by at least 2-fold, at least 3-fold, at least 4-fold, at least 5-fold, at least 6-fold, at least 7-fold, at least 8-fold, at least 9-fold, or at least 10-fold relative to the eTILs.

In some embodiments, the methods described herein may include an optional cryopreservation of eTIL and/or rTIL in a storage media (for example, media containing 5% DMSO) prior to performing an additional step desribed herein or after completion of a REP step described herein, prior to transport, thawing, and/or administration to a patient. In some embodiments, the methods described herein may include a step of thawing cryopreserved TILs (e.g. cryopreserved eTIL, cryopreserved rTIL, or a combination or mixture thereof) prior to performing an additional step described herein. In some embodiments, the additional step may be an additional or repeated expansion of the eTIL and/or rTIL (e.g., a reREP), which may be performed on the thawed cells, using, for example, a supplemented cell culture medium comprising IL-2, OKT-3, and/or feeder cells (e.g., antigen presenting cells), generally comprising peripheral blood mononuclear cells (PBMCs; or, alternatively, using antigen presenting cells), wherein the additional expansion step may be performed for at least 14 days. In some embodiments, such media may also contain combinations of IL-2, IL-15, and/or IL-23 rather than IL-2 alone.

As discussed herein, cryopreservation can occur at numerous points throughout the TIL expansion process. In some embodiments, a bulk TIL population (e.g., eTILs, rTILs, or a combination or mixture thereof) after expansion can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986. In some embodiments, the TILs described herein may be cryopreserved in 5% DMSO. In some embodiments, the TILs described herein may be cryopreserved in cell culture media plus 5% DMSO.

When appropriate, the cryopreserved cells described herein, such as cryopreserved rTILs, are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

Methods of Digesting Tumors to Obtain rTILs

In an embodiment, a method of obtaining rTILs includes a step wherein a tumor is digested using one or more enzymes. Enzymes suitable for digestion of tumors are described in Volvitz, et al., *BMC Neuroscience* 2016, 17, 30, the disclosure of which is incorporated by reference herein.

In some embodiments, the invention may include methods of obtaining rTILs that include a step wherein a tumor, which may include tumor tissue or a portion thereof, is digested using an deoxyribonuclease, a collagenase, a hyaluronidase, or a combination thereof In an embodiment, a method of obtaining rTILs includes a step wherein a tumor is digested using any enzyme that catalyzes the hydrolytic cleavage of phosphodiester linkages in the DNA backbone, thus degrading DNA. In an embodiment, a method of obtaining rTILs includes a step wherein a tumor is digested using a deoxyribonuclease (DNase). In an embodiment, a method of obtaining rTILs includes a step wherein a tumor is digested using a deoxyribonuclease and at least one other enzyme. In an embodiment, the deoxyribonuclease is deoxyribonuclease I. In an embodiment, the deoxyribonuclease is deoxyribonuclease II. In an embodiment, the deoxyribonuclease is deoxyribonuclease I from bovine pancreas (Sigma D5025 or equivalent). In an embodiment, the deoxyribonuclease is recombinant deoxyribonuclease I from bovine expressed in Pichia pastoris (Sigma D2821 or equivalent). In an embodiment, the deoxyribonuclease is recombinant human deoxyribonuclease I (rhDNAase I, also known as dornase alfa, commercially available as PULMOZYME from Genentech, Inc.). In an embodiment, the deoxyribonuclease is deoxyribonuclease II from bovine spleen (Sigma D8764 or equivalent). In an embodiment, the deoxyribonuclease is deoxyribonuclease II from porcine spleen (Sigma D4138 or equivalent). In an embodiment, any of the foregoing deoxyribonucleases is present in the tumor digest. The preparation and properties of deoxyribonucleases suitable for use in the invention are described in U.S. Pat. Nos. 5,783,433; 6,391,607; 7,407,785; and 7,297,526, and International Patent Application Publication No. WO 2016/108244 A1, the disclosures of each of which are incorporated by reference herein.

In an embodiment, a method of obtaining rTILs includes a step wherein a tumor is digested using any enzyme that catalyzes the cleavage of peptide linkages in collagen, thus degrading collagen. In an embodiment, a method of obtaining rTILs includes a step wherein a tumor is digested using a collagenase. In an embodiment, a method of obtaining rTILs includes a step wherein a tumor is digested using a collagenase and at least one other enzyme. In an embodiment, the collagenase is collagenase from *Clostridium histolyticum*. In an embodiment, the collagenase is Clostridiopeptidase A. In an embodiment, the collagenase is collagenase I. In an embodiment, the collagenase is collagenase II. In an embodiment, the collagenase is collagenase from *Clostridium histolyticum* (Sigma C5138 or equivalent). The preparation and properties of collagenases suitable for use in the invention are described in U.S. Pat. Nos. 3,201,325; 3,705,083; 3,821,364; 5,177,017; 5,422,261; 5,989,888; 9,211,316; the disclosures of each of which are incorporated by reference herein.

In an embodiment, a method of obtaining rTILs includes a step wherein a tumor is digested using any enzyme that catalyzes the degradation of hyaluronic acid. In an embodiment, a method of obtaining rTILs includes a step wherein a tumor is digested using a hyaluronidase. In an embodiment, a method of obtaining rTILs includes a step wherein a tumor is digested using a hyaluronoglucosidase. In an embodiment, the hyaluronidase is hyaluronidase Type I from bovine testes (Sigma H3506 or equivalent). In an embodiment, the hyaluronidase is hyaluronidase Type II from sheep testes (Sigma H2126 or equivalent). In an embodiment, the hyaluronidase is hyaluronidase Type III. In an embodiment, the hyaluronidase is hyaluronidase Type IV (Type IV-S) from bovine testes (Sigma H3884 or equivalent). In an embodiment, the hyaluronidase is hyaluronidase Type V from sheep testes (Sigma H6254 or equivalent). In an embodiment, the hyaluronidase is hyaluronidase Type VIII from bovine testes (Sigma H3757 or equivalent). In an embodiment, the hyaluronidase is recombinant human hyaluronidase (commercially available as HYLENEX from Halozyme, Inc.). The preparation and properties of hyaluronidases suitable for use in the invention are described in U.S. Pat. Nos. 4,820,516; 5,593,877; 6,057,110; 6,123,938; 7,767,429; 8,202,517; 8,431,124; and 8,431,380; the disclosures of each of which are incorporated by reference herein.

In an embodiment, a method of obtaining rTILs includes a step wherein a tumor is digested using a deoxyribonuclease and a hyaluronidase. In an embodiment, a method of obtaining rTILs includes a step wherein a tumor is digested using a deoxyribonuclease and a collagenase. In an embodiment, a method of obtaining rTILs includes a step wherein a tumor is digested using a hyaluronidase and a collagenase. In an embodiment, a method of obtaining rTILs includes a step wherein a tumor is digested using a deoxyribonuclease, a hyaluronidase, and a collagenase.

In an embodiment, a method of obtaining rTILs includes a step wherein a tumor is digested using a deoxyribonuclease and a hyaluronidase and at least one additional enzyme. In an embodiment, a method of obtaining rTILs includes a step wherein a tumor is digested using a deoxyribonuclease and a collagenase and at least one additional enzyme. In an embodiment, a method of obtaining rTILs includes a step wherein a tumor is digested using a hyaluronidase and a collagenase and at least one additional enzyme. In an embodiment, a method of obtaining rTILs includes a step wherein a tumor is digested using a deoxyribonuclease, a hyaluronidase, and a collagenase and at least one additional enzyme. In any of the foregoing embodiments, the additional enzyme is selected from the group consisting of caseinase, clostripain, trypsin, and combinations thereof.

In an embodiment, a method of obtaining rTILs includes a step wherein a tumor is digested using any enzyme described above, and further comprises the step of mechanically disrupting or fragmenting the tumor before, during, or after digestion.

In an embodiment, a method of obtaining rTILs includes a step wherein a tumor is digested using any enzyme described above, wherein the digestion is performed over a period selected from the group consisting of 15 minutes, 30 minutes, 45 minutes, 1 hour, 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, and 48 hours.

In an embodiment, a method of obtaining rTILs includes a step wherein a tumor is digested using any enzyme described above, wherein the digestion is performed over a period selected from the group consisting of about 15 minutes, about 30 minutes, about 45 minutes, about 1 hour, about 90 minutes, about 2 hours, about 3 hours, about 4 hours, about 5 hours, about 6 hours, about 7 hours, about 8 hours, about 9 hours, about 10 hours, about 11 hours, about 12 hours, about 18 hours, about 24 hours, about 36 hours, and about 48 hours.

In an embodiment, a method of obtaining rTILs includes a step wherein a tumor is digested using any enzyme described above, wherein the digestion is performed over a period selected from the group consisting of less than 15 minutes, less than 30 minutes, less than 45 minutes, less than 1 hour, less than 90 minutes, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 18 hours, less than 24 hours, less than 36 hours, and less than 48 hours.

In an embodiment, a method of obtaining rTILs includes a step wherein a tumor is digested using any enzyme described above, wherein the digestion is performed over a period selected from the group consisting of greater than 15 minutes, greater than 30 minutes, greater than 45 minutes, greater than 1 hour, greater than 90 minutes, greater than 2 hours, greater than 3 hours, greater than 4 hours, greater than 5 hours, greater than 6 hours, greater than 7 hours, greater than 8 hours, greater than 9 hours, greater than 10 hours, greater than 11 hours, greater than 12 hours, greater than 18 hours, greater than 24 hours, greater than 36 hours, and greater than 48 hours.

In an embodiment, a method of obtaining rTILs includes a step wherein a tumor is digested using any enzyme described above, wherein the digestion is performed over a period selected from the group consisting of between 30 minutes and 1 hour, between 1 hours and 2 hours, between 2 hours and 3 hours, between 3 hours and 4 hours, between 4 hours and 5 hours, between 5 hours and 6 hours, between 6 hours and 12 hours, between 12 hours and 18 hours, between 18 hours and 24 hours, and between 24 hours and 48 hours.

In an embodiment, a method of obtaining rTILs includes a step wherein a tumor is digested using any enzyme described above, wherein the digestion is performed at a temperature selected from the group consisting of about 20° C., about 25° C., about 30° C., about 35° C., about 40° C., about 45° C., about 50° C., about 55° C., about 60° C., about 65° C., about 70° C., about 75° C., and about 80° C.

In an embodiment, a method of obtaining rTILs includes a step wherein a tumor is digested using any enzyme described above, wherein the digestion is performed at a temperature selected from the group consisting of between 20° C. and 25° C., between 25° C. and 30° C., between 30° C. and 35° C., between 35° C. and 40° C., between 40° C. and 45° C., between 45° C. and 50° C., between 50° C. and about 55° C., between 55° C. and 60° C., between 60° C. and 65° C., between 65° C. and 70° C., between 70° C. and 75° C., and between 75° C. and 80° C.

In an embodiment, a method of obtaining rTILs includes a step wherein a tumor is digested using any enzyme described above, wherein the time and temperature of the digestion are each decreased if tumor remnants (after pre-REP) are digested. In an embodiment, a method of obtaining rTILs includes a step wherein a tumor is digested using any enzyme described above, wherein the time and temperature of the digestion are each increase if whole tumor fragments (without pre-REP) are digested.

Methods of Modulating rTIL to eTIL Ratio

In an embodiment, the concentration of rTILs relative to eTILs may be modulated or controlled by use of any expansion and digestion steps as described herein (including pre-REP), such that a therapeutic TIL product for use in the treatment of cancers described herein may contain a desirable rTIL to eTIL ratio. In an embodiment, the invention provides a method of removing eTILs from a mixture of eTILs and rTILs. In an embodiment, the invention provides a method of removing rTILs from a mixture of eTILs and rTILs.

In some embodiments of the methods of the invention, eTILs and/or rTILs may be added to a culture before an initial expansion step, at a first expansion step (e.g., pre-REP), and/or at a second expansion step (e.g., REP). In some embodiments of the methods of the invention, eTILS may be separately cultured according to the culture or expansion steps described herein through one, two, three, or more expansions, and added to a population of rTILS and eTILS at a selected rTIL to eTIL ratio. In some embodiments of the methods of the invention, rTILS may be separately cultured according to the culture or expansion steps described herein through one, two, three, or more expansions, and added to a population of eTILS to provide a mixture of rTILS and eTILS at a selected rTIL to eTIL ratio.

In an embodiment, eTILs prepared according to the methods described herein may be added to a population of rTILs to provide a selected rTIL to eTIL ratio in the resulting rTIL/eTIL mixture. In an embodiment, rTILs prepared according to the methods described herein may be added to a population of eTILs to provide a selected rTIL to eTIL ratio in the resulting rTIL/eTIL mixture.

In an embodiment, the invention provides a method of treating a cancer wherein the treatment comprises delivering a therapeutically effective amount of TILs to a patient, wherein the ratio of rTILs to eTILs in the TILs (e.g., a selected rTIL to eTIL ratio) is selected from the group consisting of about 0:100, about 1:99, about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 99:1, and about 100:0 rTIL to eTIL.

In an embodiment, the rTIL to eTIL ratio is adjusted using a selection method, which may be used to enrich or reduce rTILs relative to eTILs as required by the skilled artisan. In an embodiment, the selection method is based on the lack of exhaustion markers, including TIM3, LAG3, TIGIT, PD-1, and CTLA-4. In an embodiment, the selection method is based on enhanced CD69 expression. In an embodiment, the selection method is based on superior mitochondrial mass. In an embodiment, the selection method is based on a subset of cell surface proteins. In an embodiment, the selection method is based on phenotype. In an embodiment, the selection method is based on function.

In an embodiment, the rTIL to eTIL ratio is adjusted by co-culturing rTILs and eTILs in the same cell culture medium until a desirable ratio is obtained. In an embodiment, the rTIL to eTIL ratio is adjusted by co-culturing rTILs and eTILs in the same cell culture medium, including the addition of rTILs or eTILs to the cell culture medium at different timepoints during expansion, until a desirable ratio is obtained. In an embodiment, rTIL growth is preferentially expanded in the cell culture medium by addition of cytokines other than IL-2, including IL-4, IL-7, IL-15, and/or IL-21.

In an embodiment, the ratio of rTILs to eTILs (e.g., a selected rTIL to eTIL ratio) provided by the methods described herein may be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% rTIL to eTIL.

In an embodiment, the ratio of rTILs to eTILs (e.g., a selected rTIL to eTIL ratio) provided by the methods described herein may be at most 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% rTIL to eTIL.

In an embodiment, the ratio of rTILs to eTILs (e.g., a selected rTIL to eTIL ratio) provided by the methods described herein may be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% rTIL to eTIL.

Methods of Treating Cancers and Other Diseases

The rTILs and combinations of rTILs and eTILs described herein may be used in a method for treating diseases in a human. In an embodiment, they are for use in treating a hyperproliferative disorder. In some embodiments, the hyperproliferative disorder is cancer. In some embodiments, the hyperproliferative disorder is a solid tumor cancer. In some embodiments, the solid tumor cancer is selected from the group consisting of melanoma, double-refractory melanoma (i.e., melanoma refractory to at least two prior treatments including chemotherapy and checkpoint blockade), ovarian cancer, cervical cancer, non-small-cell lung cancer (NSCLC), lung cancer, bladder cancer, breast cancer, cancer caused by human papilloma virus, head and neck cancer, renal cancer, renal cell carcinoma, and sarcoma. In some embodiments, the hyperproliferative disorder is a hematological malignancy (or liquid tumor cancer). In some embodiments, the hematological malignancy is selected from the group consisting of acute myeloid leukemia, chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma. The rTILs and combinations of rTILs and eTILs described herein may also be used in treating other disorders as described herein and in the following paragraphs.

In an embodiment, the invention includes a method of treating a cancer in a patient in need of such treatment, wherein the treatment comprises delivering a therapeutically effective amount of rTILs to a patient, wherein the rTILs are prepared according a method comprising the steps of:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture; and
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof.

In an embodiment, the invention includes a method treating a cancer in a patient in need of such treatment, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture;
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof,
  (g) treating the patient with a non-myeloablative lymphodepletion regimen prior to administering the rTILs to the patient;
  (h) administering a therapeutically effective amount of rTILs to the patient; and
  (i) treating the patient with a high-dose IL-2 regimen starting on the day after administration of the rTILs to the patient.

In an embodiment, the invention includes a method treating a cancer in a patient in need of such treatment, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture;
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
  wherein the rTILs express reduced levels of a T cell exhaustion marker relative to the eTILs,
  wherein the T cell exhaustion marker is selected from the group consisting of TIM3, LAG3, TIGIT, PD-1, and combinations thereof, and
  wherein the second cell culture medium further comprises a cytokine selected from the group consisting of IL-4, IL-7, IL-15, IL-21, and combinations thereof,
  (g) treating the patient with a non-myeloablative lymphodepletion regimen prior to administering the rTILs to the patient;
  (h) administering a therapeutically effective amount of rTILs to the patient, wherein a therapeutically effective amount of eTILs are simultaneously administered to the patient in a mixture with the rTILs; and
  (i) treating the patient with a high-dose IL-2 regimen starting on the day after administration of the rTILs to the patient.

In an embodiment, the invention includes a method treating a cancer in a patient in need of such treatment, the method comprising:
  (a) obtaining tumor tissue from the patient, wherein the tumor tissue comprises tumor infiltrating lymphocytes (TILs);
  (b) fragmenting the tumor tissue;
  (c) treating the tumor tissue in a gas permeable container with a first cell culture medium and interleukin 2 (IL-2) to provide tumor remnants and emergent TILs (eTILs);
  (d) removing at least a plurality of the eTILs;
  (e) enzymatically digesting the tumor remnants into tumor remnant cells using a digest mixture;
  (f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein the second cell culture medium further comprises a cytokine selected from the group consisting of IL-4, IL-7, IL-15, IL-21, and combinations thereof, (g) treating the patient with a non-myeloablative lymphodepletion regimen prior to administering the rTILs to the patient;

(h) administering a therapeutically effective amount of rTILs to the patient, wherein a therapeutically effective amount of eTILs are simultaneously administered to the patient in a mixture with the rTILs; and (i) treating the patient with a high-dose IL-2 regimen starting on the day after administration of the rTILs to the patient, wherein the cancer is selected from the group consisting of melanoma, double-refractory melanoma, ovarian cancer, cervical cancer, lung cancer, bladder cancer, breast cancer, head and neck cancer, renal cell carcinoma, acute myeloid leukemia, colorectal cancer, sarcoma, non-small cell lung cancer (NSCLC), and triple negative breast cancer.

In an embodiment, the invention includes a method treating a cancer in a patient in need of such treatment, the method comprising:

(a) obtaining tumor tissue from the patient, wherein the tumor tissue comprises tumor infiltrating lymphocytes (TILs);

(b) fragmenting the tumor tissue;

(c) treating the tumor tissue in a gas permeable container with a first cell culture medium and interleukin 2 (IL-2) to provide tumor remnants and emergent TILs (eTILs);

(d) removing at least a plurality of the eTILs;

(e) enzymatically digesting the tumor remnants into tumor remnant cells using a digest mixture;

(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);

wherein the rTILs express reduced levels of a T cell exhaustion marker relative to the eTILs, wherein the T cell exhaustion marker is selected from the group consisting of TIM3, LAG3, TIGIT, PD-1, and combinations thereof, and wherein the second cell culture medium further comprises a cytokine selected from the group consisting of IL-4, IL-7, IL-15, IL-21, and combinations thereof, (g) treating the patient with a non-myeloablative lymphodepletion regimen prior to administering the rTILs to the patient, wherein the non-myeloablative lymphodepletion regimen comprises the steps of administration of cyclophosphamide at a dose of 60 mg/m²/day for two days followed by administration of fludarabine at a dose of 25 mg/m²/day for five days;

(h) administering a therapeutically effective amount of rTILs to the patient, wherein a therapeutically effective amount of eTILs are simultaneously administered to the patient in a mixture with the rTILs; and (i) treating the patient with a high-dose IL-2 regimen starting on the day after administration of the rTILs to the patient.

In some embodiments of the methods described herein, the step of removing at least a plurality of the eTILs includes removing at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% of the eTILs.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

Co-Administration of IL-2

In an embodiment, the invention provides a method of treating a cancer in a patient in need of such treatment, comprising the steps of:

(a) obtaining rTILs from a tumor resected from a patient according to a method described herein;

(b) treating the patient with a non-myeloablative lymphodepletion regimen prior to administering the rTILs to the patient;

(c) administering a therapeutically effective amount of rTILs to the patient; and (d) treating the patient with an IL-2 regimen starting on the day after administration of the rTILs to the patient.

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the third population of TILs, wherein the aldesleukin or a biosimilar or variant thereof is administered at a dose of 600,000 or 720,000 IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the third population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a high-dose IL-2 regimen starting on the day after administration of the rTILs to the patient,
wherein the high-dose IL-2 regimen comprises 600,000 or 720,000 IU/kg of aldesleukin, or a biosimilar or variant thereof, administered as a 15-minute bolus intravenous infusion every eight hours until tolerance.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises $18 \times 10^6$ IU/m$^2$ administered intravenously over 6 hours, followed by $18 \times 10^6$ IU/m$^2$ administered intravenously over 12 hours, followed by $18 \times 10^6$ IU/m$^2$ administered intravenously over 24 hours, followed by $4.5 \times 10^6$ IU/m$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof,
(g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a decrescendo IL-2 regimen starting on the day after administration of the rTILs to the patient,
wherein the decrescendo IL-2 regimen comprises $18 \times 10^6$ IU/m$^2$ administered intravenously over 6 hours, followed by $18 \times 10^6$ IU/m$^2$ administered intravenously over 12 hours, followed by $18 \times 10^6$ IU/m$^2$ administered intravenously over 24 hours, followed by $4.5 \times 10^6$ IU/m$^2$ administered intravenously over 72 hours, repeated every 28 days for a maximum of four cycles.

In an embodiment, the IL-2 regimen comprises administration of pegylated IL-2, including pegylated aldesleukin. In an embodiment, the IL-2 regimen comprises administration of pegylated IL-2 every 1, 2, 4, 6, 7, 14 or 21 days at a dose of 0.10 mg/day to 50 mg/day.

In an embodiment, the invention includes a method treating a cancer in a patient in need of such treatment, the method comprising:
(a) obtaining tumor tissue from the patient, wherein the tumor tissue comprises tumor infiltrating lymphocytes (TILs);
(b) fragmenting the tumor tissue;
(c) treating the tumor tissue in a gas permeable container with a first cell culture medium and interleukin 2 (IL-2) to provide tumor remnants and emergent TILs (eTILs);
(d) removing at least a plurality of the eTILs;
(e) enzymatically digesting the tumor remnants into tumor remnant cells using a digest mixture;
(f) expanding the tumor remnant cells with a second cell culture medium comprising cell culture media, irradiated feeder cells, OKT-3 antibody, and IL-2 in a gas permeable container to provide an expanded number of remnant tumor infiltrating lymphocytes (rTILs);
wherein the rTILs express reduced levels of a T cell exhaustion marker relative to the eTILs,
wherein the T cell exhaustion marker is selected from the group consisting of TIM3, LAG3, TIGIT, PD-1, and combinations thereof, and
wherein the second cell culture medium further comprises a cytokine selected from the group consisting of IL-4, IL-7, IL-15, IL-21, and combinations thereof, (g) treating the patient with a non-myeloablative lymphodepletion regimen prior to administering the rTILs to the patient;
(h) administering a therapeutically effective amount of rTILs to the patient, wherein a therapeutically effective amount of eTILs are simultaneously administered to the patient in a mixture with the rTILs; and
(i) treating the patient with a pegylated IL-2 regimen starting on the day after administration of the rTILs to the patient,
wherein the pegylated IL-2 regimen comprises administration of pegylated IL-2 every 1, 2, 4, 6, 7, 14 or 21 days at a dose of 0.10 mg/day to 50 mg/day.

Non-Myeloablative Lymphodepletion with Chemotherapy

In an embodiment, the invention includes a method of treating a cancer with a population of rTILs, wherein a patient is pre-treated with non-myeloablative chemotherapy prior to an infusion of rTILs according to the invention. In some embodiments, the population of rTILs may be provided with a population of eTils, wherein a patient is pre-treated with non-myeloablative chemotherapy prior to an infusion of rTILs and eTils according to the invention. In an embodiment, the non-myeloablative chemotherapy is cyclophosphamide 60 mg/kg/d for 2 days (days 27 and 26 prior to rTIL infusion) and fludarabine 25 mg/m$^2$/d for 5 days (days 27 to 23 prior to rTIL infusion). In an embodiment, after non-myeloablative chemotherapy and rTIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.*, 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide are together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

Pharmaceutical Compositions, Dosages, and Dosing Regimens

In an embodiment, rTILs expanded using methods of the invention are administered to a patient as a pharmaceutical composition. In an embodiment, the pharmaceutical composition is a suspension of rTILs in a sterile buffer. rTILs expanded using methods of the invention may be administered by any suitable route as known in the art. Preferably, the rTILs are administered as a single intra-arterial or intravenous infusion, which preferably lasts approximately 30 to 60 minutes. Other suitable routes of administration include intraperitoneal, intrathecal, and intralymphatic administration.

In an embodiment, rTILs and eTILs expanded using methods of the invention are administered to a patient as a pharmaceutical composition. In an embodiment, the pharmaceutical composition is a suspension of rTILs and eTILs in a sterile buffer. rTILs and eTILs expanded using methods of the invention may be administered by any suitable route as known in the art. Preferably, the rTILs and eTILs are administered as a single intra-arterial or intravenous infusion, which preferably lasts approximately 30 to 60 minutes. Other suitable routes of administration include intraperitoneal, intrathecal, and intralymphatic administration.

Any suitable dose of rTILs can be administered. Preferably, from about $2.3 \times 10^{10}$ to about $13.7 \times 10^{10}$ rTILs are administered, with an average of around $7.8 \times 10^{10}$ rTILs, particularly if the cancer is melanoma. In an embodiment, about $1.2 \times 10^{10}$ to about $4.3 \times 10^{10}$ of rTILs are administered.

Any suitable dose of rTILs and eTILs can be administered. Preferably, from about $2.3 \times 10^{10}$ to about $13.7 \times 10^{10}$ rTILs and eTILs are administered, with an average of around $7.8 \times 10^{10}$ rTILs and eTILs, particularly if the cancer is melanoma. In an embodiment, about $1.2 \times 10^{10}$ to about $4.3 \times 10^{10}$ of rTILs and eTILs are administered.

In some embodiments, the number of the rTILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the rTILs provided in the pharmaceutical compositions of the invention is in the range of $1 \times 10^{6}$ to $5 \times 10^{6}$, $5 \times 10^{6}$ to $1 \times 10^{7}$, $1 \times 10^{7}$ to $5 \times 10^{7}$, $5 \times 10^{7}$ to $1 \times 10^{8}$, $1 \times 10^{8}$ to $5 \times 10^{8}$, $5 \times 10^{8}$ to $1 \times 10^{9}$, $1 \times 10^{9}$ to $5 \times 10^{9}$, $5 \times 10^{9}$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the number of the rTILs and eTILs provided in the pharmaceutical compositions of the invention is about $1 \times 10^{6}$, $2 \times 10^{6}$, $3 \times 10^{6}$, $4 \times 10^{6}$, $5 \times 10^{6}$, $6 \times 10^{6}$, $7 \times 10^{6}$, $8 \times 10^{6}$, $9 \times 10^{6}$, $1 \times 10^{7}$, $2 \times 10^{7}$, $3 \times 10^{7}$, $4 \times 10^{7}$, $5 \times 10^{7}$, $6 \times 10^{7}$, $7 \times 10^{7}$, $8 \times 10^{7}$, $9 \times 10^{7}$, $1 \times 10^{8}$, $2 \times 10^{8}$, $3 \times 10^{8}$, $4 \times 10^{8}$, $5 \times 10^{8}$, $6 \times 10^{8}$, $7 \times 10^{8}$, $8 \times 10^{8}$, $9 \times 10^{8}$, $1 \times 10^{9}$, $2 \times 10^{9}$, $3 \times 10^{9}$, $4 \times 10^{9}$, $5 \times 10^{9}$, $6 \times 10^{9}$, $7 \times 10^{9}$, $8 \times 10^{9}$, $9 \times 10^{9}$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the rTILs and eTILs provided in the pharmaceutical compositions of the invention is in the range of $1 \times 10^{6}$ to $5 \times 10^{6}$, $5 \times 10^{6}$ to $1 \times 10^{7}$, $1 \times 10^{7}$ to $5 \times 10^{7}$, $5 \times 10^{7}$ to $1 \times 10^{8}$, $1 \times 10^{8}$ to $5 \times 10^{8}$, $5 \times 10^{8}$ to $1 \times 10^{9}$, $1 \times 10^{9}$ to $5 \times 10^{9}$, $5 \times 10^{9}$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the rTILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the rTILs and eTILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the rTILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the rTILs and eTILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the rTILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the rTILs and eTILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the rTILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the concentration of the rTILs and eTILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the rTILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the rTILs and eTILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the rTILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the rTILs and eTILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The rTILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the rTILs may also be used if appropriate. The amounts of the pharmaceutical compositions administered using the methods herein, such as the dosages of rTILs, will be dependent on the human or mammal being treated, the severity of the disorder or condition, the rate of administration, the disposition of the active pharmaceutical ingredients and the discretion of the treating physician.

The rTILs and eTILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the rTILs and eTILs may also be used if appropriate. The amounts of the pharmaceutical compositions administered using the methods herein, such as the dosages of rTILs and eTILs, will be dependent on the human or mammal being treated, the severity of the disorder or condition, the rate of administration, the disposition of the active pharmaceutical ingredients and the discretion of the treating physician.

In some embodiments, rTILs may be administered in a single dose. Such administration may be by injection, e.g., intravenous injection. In some embodiments, rTILs may be administered in multiple doses. Dosing may be once, twice, three times, four times, five times, six times, or more than six times per year. Dosing may be once a month, once every two weeks, once a week, or once every other day. Administration of rTILs may continue as long as necessary.

In some embodiments, rTILs and eTILs may be administered in a single dose. Such administration may be by injection, e.g., intravenous injection. In some embodiments, rTILs may be administered in multiple doses. Dosing may be once, twice, three times, four times, five times, six times, or more than six times per year. Dosing may be once a month, once every two weeks, once a week, or once every other day. Administration of rTILs and eTILs may continue as long as necessary.

In some embodiments, an effective dosage of rTILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of rTILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of rTILs and eTILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of rTILs and eTILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of rTILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of rTILs and eTILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of rTILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

In some embodiments, an effective dosage of rTILs and eTILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the rTILs and/or eTILs may be administered in either single or multiple doses by any of the accepted modes of administration of agents having similar utilities, including by infusion into the bloodstream, infusion into a tumor, intra-arterial injection, intravenously, intraperitoneally, parenterally, intramuscularly, subcutaneously, topically, by intranasal administration, by transplantation, or by inhalation.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1

Expansion of rTILs from Tumor Digests

Tumor remnants were digested according to the following exemplary procedure. This procedure describes the digestion of a fresh human tumor sample into a viable, single-cell suspension, to obtain and isolate tumor-infiltrating lymphocytes, and may use DNase-Collagenase-Hyaluronidase (DCH) methods (as described herein) or MACS human tumor dissociation kit (TDK) (Miltenyi Biotech, Inc., San Diego, Calif., USA) digestion protocols for the dissociation of human tumors.

Preparation of the CM1+IL-2 working culture medium is as follows. Place 500 mL RPMI 1640, 200 mM L-glutamine, and 100 mL human AB serum in a water bath at 37° C. to equilibrate for at least 30 minutes. Transfer the contents of this mixture from the water bath to a biosafety cabinet along with 1000× β-ME stock and 50 mg/mL gentamicin stock solution from the refrigerator. Remove 50 mL from the RPMI 1640, add: 50 mL human AB serum, 5 mL 200 mM L-glutamine, 500 μL 1000× β-ME, and 500 μL 50 mg/mL gentamicin. To complete medium 1, add 500 μL of 6000 U/mL reconstituted human rhIL-2 (CellGenix, Inc., Portsmouth, N.H., USA).

The 10× DCH stock solution is prepared using the following procedure, which is depicted in FIG. 1. First, the volume required to reconstitute each enzyme to obtain the desired working solution concentrations is calculated. For example, reconstitute 150,000 U (international units) of deoxyribonuclease in 15 mL to obtain a 10,000 U/mL working solution. Aliquot leftover working solution. Reconstitute the lyophilized enzymes in an amount of sterile Hanks' balanced salt solution (HBSS, Sigma H6648, Sigma-Aldrich Co., St. Louis, Mo., USA, or equivalent) previously calculated above at room temperature. Remove any residual powder from the sides of the bottles and from the protective foil. Pipette up and down several times and swirl to ensure complete reconstitution. Add 100,000 U of DNase (deoxyribonuclease I from bovine pancreas, Sigma D5025 or equivalent), 1 g of collagenase (Sigma C5138 from *Clostridium histolyticum* or equivalent), and 100 mg of hyaluronidase (Type V from sheep testes, Sigma H6254 or equivalent) to a final volume of 100 mL sterile HBSS to obtain a 10× triple enzyme digestion stock solution for human tumors. Aliquot the remaining enzyme working solutions into 10,000 U/mL DNase, 10 mg/mL collagenase and 1 mg/mL hyaluronidase. The 10× DCH stock solution at 100 mL final volume has the following concentrations: DNase I 1000 U/mL, collagenase 10 mg/mL, and hyaluronidase 1 mg/mL. The 10× DCH stock solution is diluted to 1× DCH in HBSS for tumor digestion.

Concurrently, for comparison of the DCH digest with MACS TDK, prepare the reagents included in the MACS TDK to manufacturer specifications, if desired. Thaw aliquots that have been stored at −20° C. at room temperature.

The tumor may be prepared for digestion as follows. Remove the tumor from its primary and secondary packaging and weigh the vial, record the mass, and transfer to a biosafety cabinet. Cut the tumor into fragments, or morcellate the tumor. Several fragments are selected to be used in the digestion protocol, and additional fragments are retained for histology and DNA extractions if desired.

Figure 2:
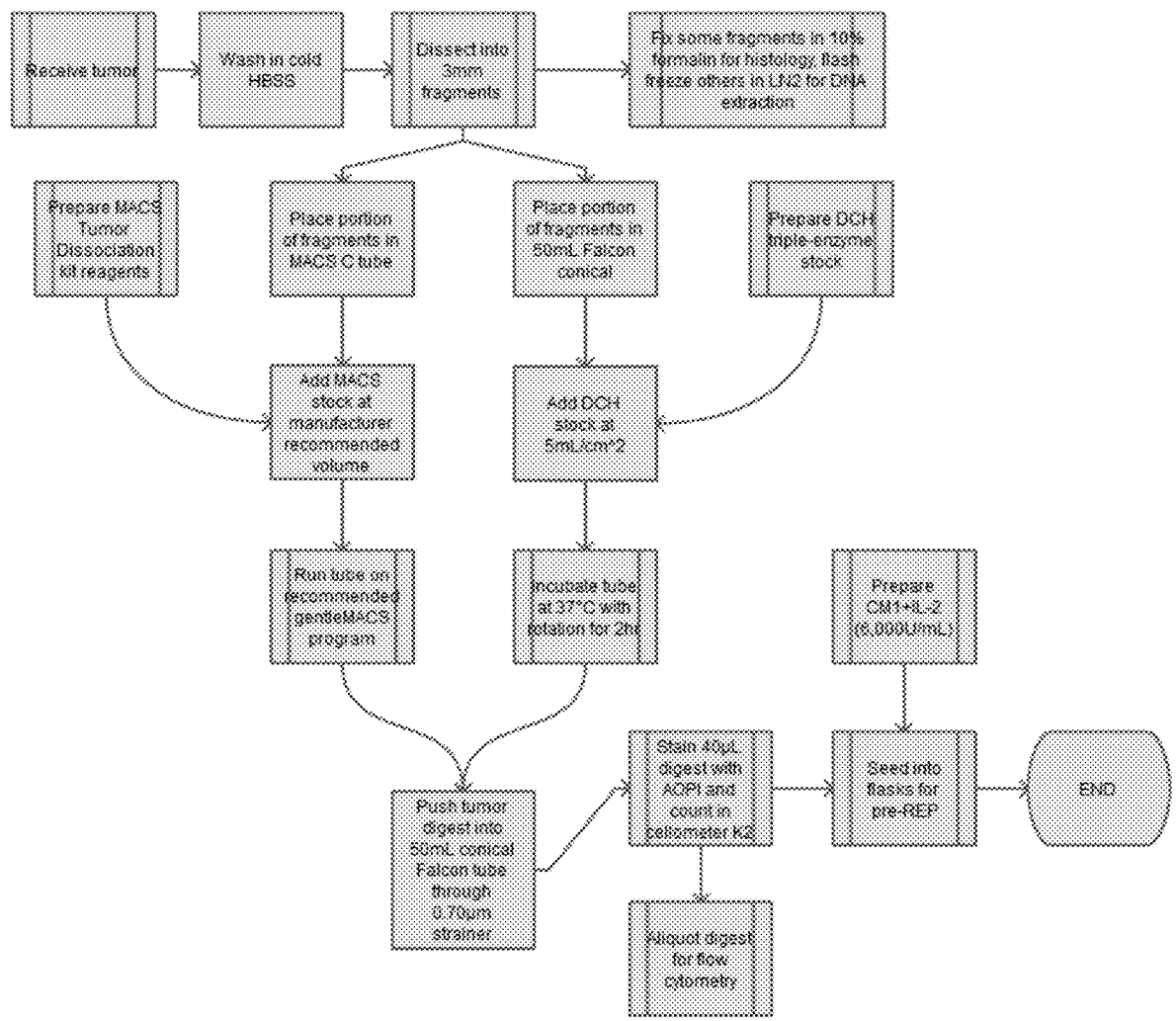
FIG. 2 illustrates an exemplary flow-through diagram of the tumor digestion procedure. In this example, two digestion methods are performed simultaneously and are seeded separately as a part of two distinct pre-REPs designed to compare the efficacy of each digestion method.

An exemplary DCH-based tumor digestion procedure is depicted in FIG. 2 and includes the following steps. The 10× DCH stock solution must be diluted to a 1× working concentration for digestions. Calculate the total volume needed for the digestion of the tumor, which is about 5 mL of solution per $cm^2$ of tumor. Dilute the DCH working solution to 1× by adding 1 part DCH to 9 parts HBSS. Transfer tumor fragments to a 50 mL Flacon conical tube in the volume of HBSS calculated above. Add the amount of 10× DCH calculated above, cap the tube, and optionally seal. Transfer to the MACS tube rotator (Miltenyi Biotech, Inc., San Diego, Calif., USA) in a 37° C., 5% $CO_2$ humidified incubator on constant rotation for 1 to 2 hours. Alternatively, the tumor fragments can be digested at room temperature overnight, also with constant rotation. Attach a 0.70 μm strainer to sterile Falcon conical tube. Obtain the digestion from the incubator and using a pipette, and add all contents of the digestion to the strainer. Use the butt of a sterile syringe plunger to push any solid through the strainer. The tube is capped and contains DCH-digested rTILs. The cells may be washed to remove the digest cocktail, counted, and resuspended in media for REP expansion as described elsewhere herein.

If a pre-REP step is desired to provide eTILs for comparison with rTILs (as in the following Examples), seed G-REX flasks for pre-REP using the DCH-digested rTILs. Label the necessary number of G-REX 10 flasks and add the digest. Add CM1+IL-2 to obtain 40 mL final volume. Place the flasks in a 5% $CO_2$ incubator at 37° C. with humidity. Cell counting and viability may be performed using a Nexcelom Cellometer K2 using 40 μL of sample to 40 μL of acrydine orange and propidium iodide dual staining solution (AOPI) solution, and count in duplicate for each digest or condition, diluting as needed. Mix samples well to avoid clumping, and pipette AOPI promptly before running each sample to ensure viability isn't obfuscated by the cytotoxic effect of propidium iodide.

The DCH procedure described above was found to be surprisingly superior to the MACS TDK enzymatic digest mixture and procedure for several reasons. Three independent experiments using the MACS TDK mixture were performed. The first experiment was performed using a melanoma tumor, where a significant downregulation of the $CD4^+/CD8^+$ population in rTILs was observed by flow cytometry using the MACS system. Such an effect was not observed in DCH-digested rTILs, indicating that the MACS digest procedure may adversely affect the expression of surface markers. In a second experiment, an estrogen receptor-positive (ER+)/progesterone receptor-positive (PR+) breast tumor was used, and the MACS digest let to the appearance of debris in the 24-well G-REX plate, whereas the DCH digest did led to clear material, indicating poor digestion for the MACS enzyme cocktail. Finally, a second digest of a different ER+/PR+ breast tumor using the MACS TDK enzymatic digest mixture and procedure led to both poor yield and viability of rTILs.

Example 2

Phenotypic Characterization of rTILs from Tumor Digests

During the pre-REP, tumor-resident TILs emigrate as eTILs and proliferate. The length of the pre-REP used to prepare eTILs for comparison with rTILs may vary between 11-21 days, depending on cell growth. Residual tumor fragments (remnants) are normally discarded and the expanded eTIL are subjected to a REP with irradiated PBMC feeders, anti-CD3 and IL-2. Viable TILs remaining in the tumor remnants (rTILs) following the pre-REP were investigated after digestion according to Example 1 as described above to assess their function and phenotype in comparison to eTILs.

Cell populations from the tumor remnants and pre-REP suspension (i.e., the expanded cell population) in melanoma, head and neck, breast, renal, pancreatic, lung and colorectal tumors (n=17) were evaluated and compared. Interestingly, rTILs are consistently phenotypically distinct from eTILs, as determined herein and shown by differential expression of various markers including LAG3, TIM-3, PD-1, CD69, CD45RO, CD27, CD56, CD57 and HLA-DR. A REP of the tumor remnant and pre-REP populations resulted in comparable expansion, but similar to the pre-REP results, the phenotypic signature varied between the two populations with respect to LAG3, TIM-3, HLA-DR and CD28.

The rTIL and eTIL obtained from melanoma, breast, renal, pancreatic, lung and colorectal tumors (n=9) were evaluated and compared. Tumor rTIL are consistently phenotypically distinct from eTIL, as determined by differential expression of various markers (Table 3 and FIG. 3).

TABLE 3

Summary of phenotypic characterization results for nine tumors.

| | Marker Expression | | | | | | | |
|---|---|---|---|---|---|---|---|---|
| | LAG3 ($CD8^+/CD4^+$) MFI | TIM3 ($CD8^+/CD4^+$) MFI | PD-1 $CD8^+/CD4^+$ % | CD69 $CD8^+/CD4^+$ MFI | CD154 ($CD8^+/CD4^+$) MFI | CD28 ($CD8^+/CD4^+$) MFI | CD57 ($CD8^+/CD4^+$) % | CD56 % |
| eTIL | 507/ 144 | 2832/ 1756 | 36.95/ 47 | 1320/ 1543 | 1498/ 3751 | 1163/ 5036 | 18.76/ 19.6 | 5.615 |
| rTIL | 209/ 106 | 877/ 742 | 42.8/ 48 | 3437/ 223.4 | 1034/ 1167 | 458.3/ 2795 | 9.16/ 8.5 | 1.027 |
| *P-values (CD8/CD4) | 0.05/ 0.21 | 0.05/ 0.01 | 0.38/ 0.89 | 0.11/ 0.001 | 0.55/ 0.01 | 0.05/ 0.11 | 0.05/ 0.06 | 0.05 |

*P-values represent the difference between rTIL and eTIL using students unpaired T test.

The fundamental differences in rTILs as compared to eTILs were increased CD69 expression (7-fold median fluorescence intensity (MFI) in CD4$^+$) (p<0.0001), diminished LAG3 expression (2-fold MFI in CD8$^+$ T cells) (p<0.05) and TIM3 expression (3- and 2-fold MFI in CD8$^+$ and CD4$^+$ T cells, respectively) (p<0.05/0.01), diminished CD154 expression (3-fold MFI in CD4$^+$ T cells) (p<0.01), and diminished CD56 expression (5%) (p<0.05). Surprisingly, a REP of rTILs and eTILs resulted in comparable expansion, similar to the pre-REP results, as described in Example 4. The phenotypic signature of rTILs was sustained after REP with fidelity with of expression to the individual levels of LAG3, TIM3, and CD28, as described in Example 4. Furthermore, since CD57 is a receptor associated with terminal differentiation, the results suggest that rTILs are less terminally differentiated than eTILs (i.e., less likely to die).

Figure 3:
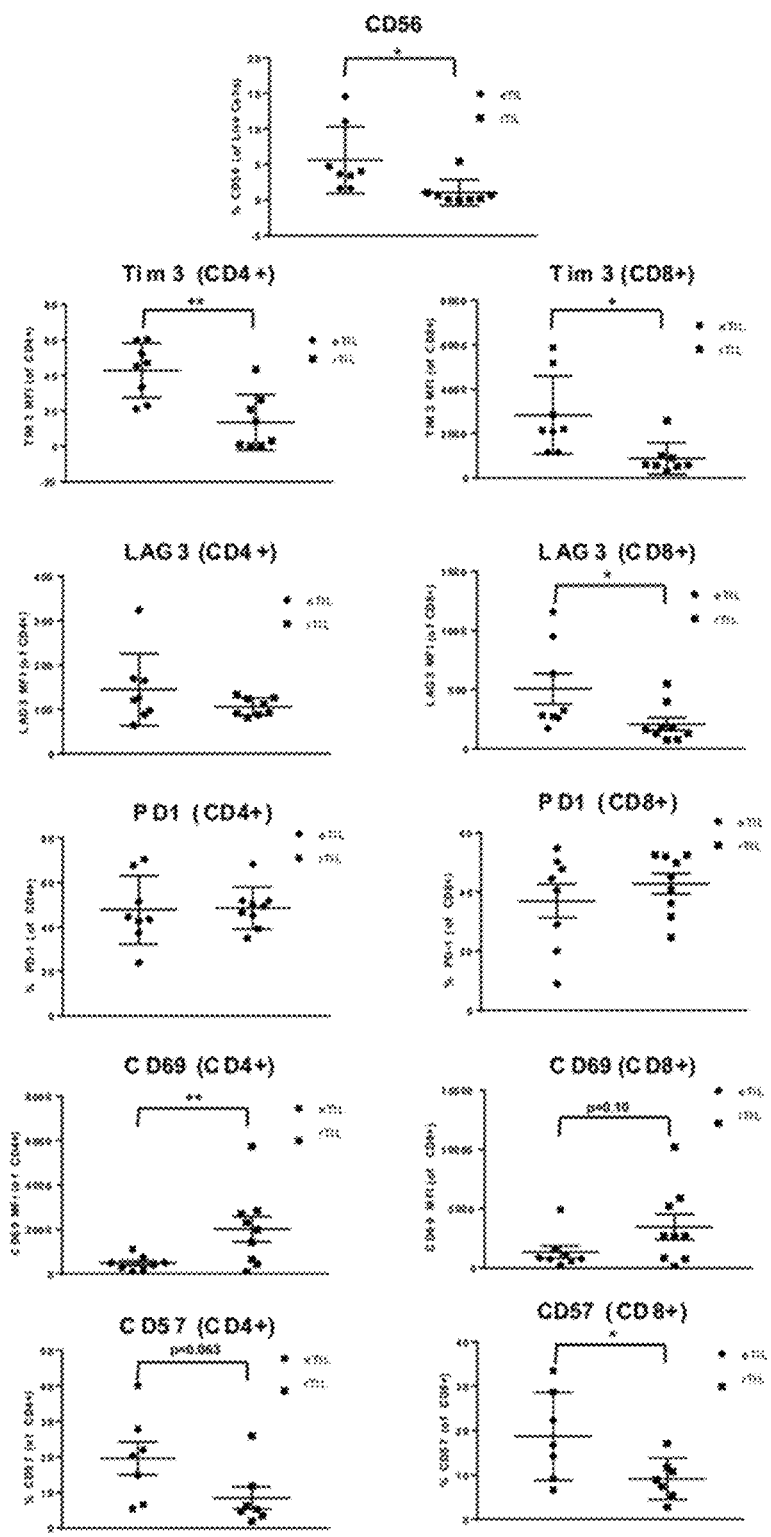
FIG. 3 illustrates differential phenotypic expression of key markers in eTILs and rTILs.

The results reported in FIG. 3 and Table 3 show that eTIL and rTIL exhibit distinct yet consistent differences in phenotypic expression in various tumor histologies. Most notably, there was a reduction in the expression of the so called "exhaustion markers" (LAG3 and TIM3) in the rTIL. Interestingly, PD-1 was similarly expressed in the eTIL and rTIL. Additionally, there was an enhancement in CD69 expression in the rTIL, compared to the eTIL, yet KLRG1 was similar between the two populations (data not shown). This provides further evidence that the rTIL do not appear to be terminally differentiated, but phenotypically resemble tissue-resident effector memory T cells.

Collectively, these results have identified significant differences in the biology of cell populations that remain in the tumor or expand and progress out of the tumor, and the signals associated with emigration and retention.

Example 3

Functional Characterization of rTILs from Tumor Digests

Figure 4:
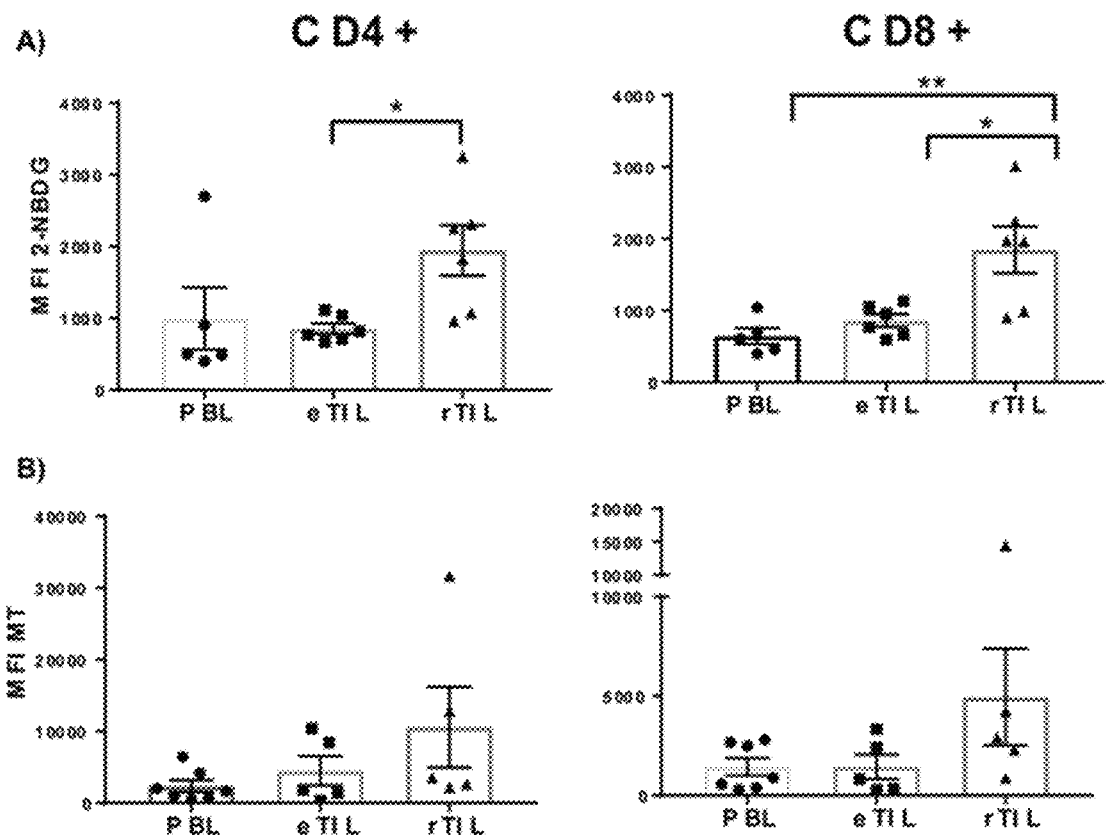
FIG. 4 illustrates studies of eTIL and rTIL by 2-(N-(7-nitrobenz-2-oxa-1,3-diazol-4-yl)amino)-2-deoxyglucose (2-NBDG) (A) and Mitotracker (B) to assess metabolic capacity prior to rapid expansion.

T cell dysfunction is directly associated with a loss of mitochondrial function. Sharping, et al., *Immunity* 2016, 45, 374-88. Moreover, the reprogramming of T cells to favor mitochondrial biogenesis can increase intratumoral T cell persistence and function. Therefore, more metabolically active T cells are pivotal in mounting an efficient immune response to tumor. In an effort to assess the eTIL and rTIL functionally, eTIL and rTIL were compared in terms of metabolic capacity via Mitotracker and 2-(N-(7-nitrobenz-2-oxa-1,3-diazol-4-yl)amino)-2-deoxyglucose (2-NBDG). 2-NBDG may be used to measure glucose uptake, but does not specify the primary metabolic process; i.e., full oxidation in the mitochondria or only glycolysis and generation of lactate. Mitotracker dye (ThermoFisher Scientific, Inc., Waltham, Mass., USA) may be used to measure mitochondrial mass. Comparison of the eTIL and rTIL by this approach demonstrated an enhancement in glucose update in the rTIL, as shown in FIG. 4. This result is surprising because rTILs, being directly liberated from the tumor, are expected to be more glycolytic; however, when the mitochondrial mass the rTILs was assessed, they exhibited a slightly enhanced level of Mitotracker compared to the eTIL. These results demonstrate that rTIL were more metabolically active than eTIL, when expected to be less active, and suggest that the rTIL may have a greater capacity to amount an immune response to tumor than eTIL.

Figure 5:
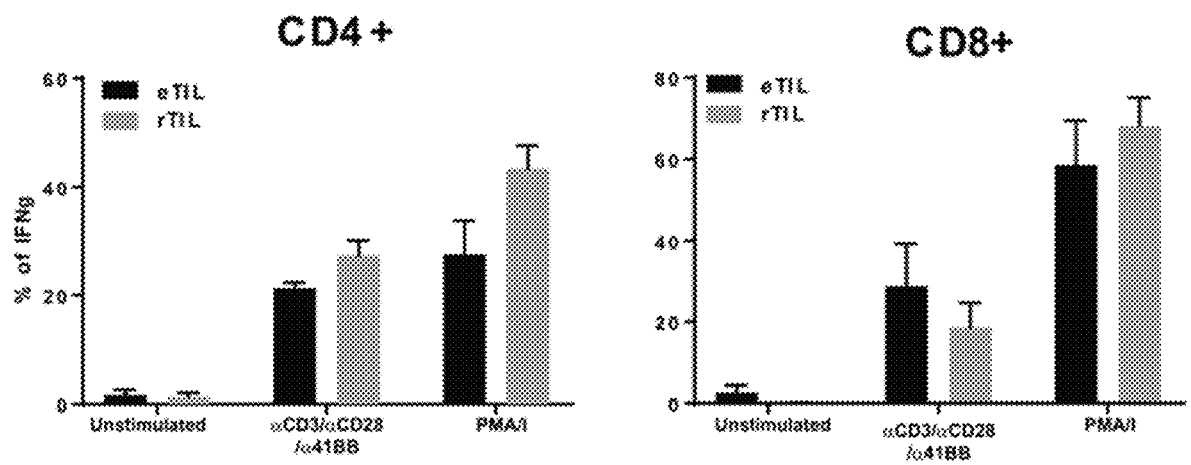
FIG. 5 shows the results of experiments wherein eTIL and rTIL were stimulated with CD3/CD28/4-1BB beads with brefeldin A overnight for CD4$^+$ and CD8$^+$ T cells. PMA and ionomycin was added for 4-5 hours. Interferon-γ was assessed by intracellular flow cytometric analysis (n=3).

To further assess their functional capabilities, rTILs were stimulated overnight with brefeldin A and beads coated with anti-CD3, anti-CD28, and anti-CD137 antibodies (DYNABEADS, catalog no. 11162D, commercially available from ThermoFisher Scientific, Inc., Waltham, Mass., USA) and IFN-γ was measured. Cells were harvested and stained intracellularly for IFN-γ following permeabilization and assessed by flow cytometry. The results are shown in FIG. 5.

Cells were also stimulated with phorbol 12-myristate 13-acetate (PMA) and ionomycin to evaluate the capability of TILs to produce cytokine. The results are also shown in FIG. 5. Granzyme B, TNF-α and IL-17A levels were also assessed. There was negligible IL-17A, and no differences in TNFα or granzyme B between rTILs and eTILs (data not shown). Surprisingly, a slightly elevated level of IFN-γ in the CD4$^+$ subset (but not in CD8$^+$ T cells) was observed (n=3) in the anti-CD3/anti-CD28/anti-CD137 bead and PMA/ionomycin conditions in rTILs compared to eTILs. This data suggests that rTILs are functionally competent cells, and show evidence of greater functional competence that eTILs.

Example 4

Figure 6:
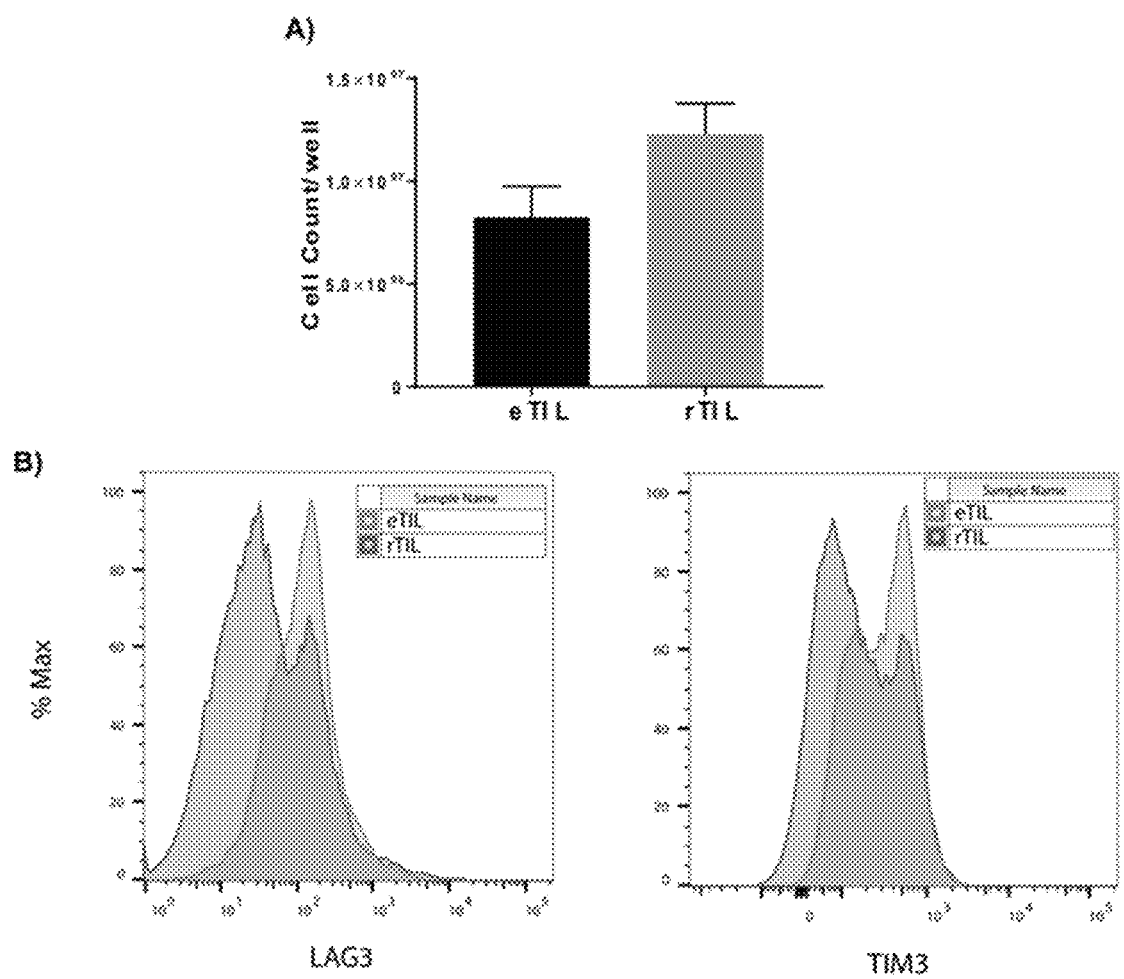
FIG. 6 illustrates results showing that (A) rTIL expand and (B) remain phenotypically distinct from eTIL during rapid expansion.

Comparison of REP of rTILs and eTILs from Tumor Digests eTILs and rTILs were subjected to a rapid expansion protocol (REP) with irradiated PBMC feeders, anti-CD3 antibody (OKT3), and IL-2 for 14 days. Viability and cells counts were assessed in duplicate in 3 independent tumors (n=3). Phenotypic expression was assessed by flow cytometry. Successful initiation in mini-REP experiments was observed for both rTILs and eTILs. The REP performance of the TILs with anti-CD3 antibody and feeders was similar (FIG. 6A), although the rTILs surprisingly exhibited a slightly enhanced number of cells (p<0.08), compared to the eTIL. As observed prior to REP (see Example 2), the eTILs and rTILs obtained post-REP were phenotypically distinct. Many of the phenotypic differences observed in the pre-REP were preserved during the REP, such as a reduction in LAG3 and TIM3 expression in the rTIL (FIG. 6B).

Additional properties of eTILs and rTILs may be compared based on the results of (1) deep TCR sequencing, (2) co-culture proliferation (rTIL/eTIL co-culture with cytokine mixtures) and additional functional assays, (3) assays for transcriptional profiling (e.g., using a NanoString Technologies NCOUNTER system). TCR sequencing may assess the clonality and/or diversity of the TCR repertoire, including Vb repertoire. Telomere length may also be assessed to compare rTILs to eTILs.

Example 5

Treatment of Human Disease with rTILs and Combinations of rTILs and eTILs

Figure 7:
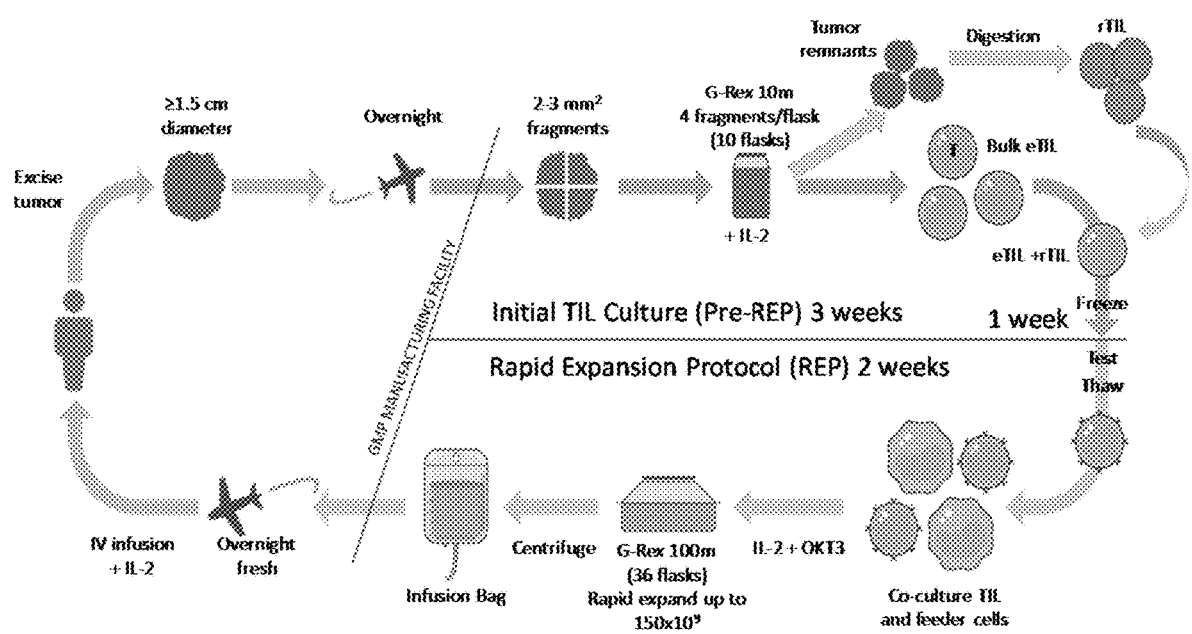
FIG. 7 illustrates an exemplary process for treating a patient using rTILs of the invention.

The rTILs of the invention may be used in the treatment of cancers as described herein. An overall process flow diagram for the expansion of rTILs from a patient tumor and treatment of a patient is depicted in FIG. 7. The process allows for tailoring of the rTIL to eTIL ratio in the TIL product infused to the patient as shown. The ratio of rTIL to eTIL may be selected by way of an affinity assay or other cell sorting assay known by persons having ordinary skill in the art based on the differential expression of CD69 and/or T-cell exhaustive markers in rTILs and eTILs.

Figure 8:
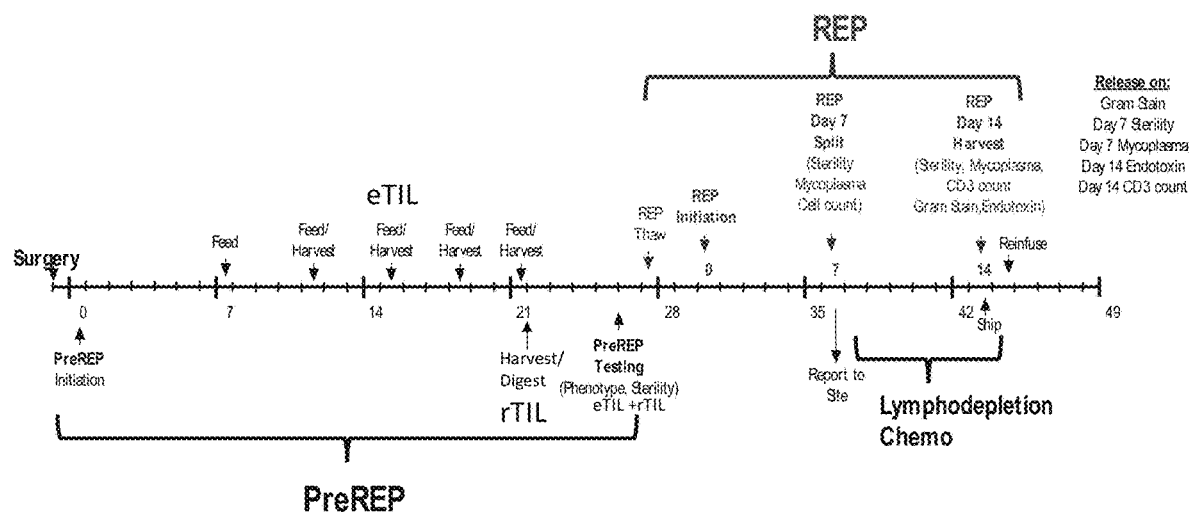
FIG. 8 illustrates an exemplary timeline of the process for treating a patient using rTILs of the invention.

In FIG. 8, a timeline showing an exemplary process of obtaining rTILs from a patient tumor, expanding the rTILs from tumor remnants after pre-REP using a REP stage, performing lymphodepletion, and infusion of rTILs into a patient is shown in conjunction with a parallel eTIL process.

Example 6

Study to Assess the VP Repertoire in eTIL and rTIL

The eTIL and rTIL were assessed for differences in the VP T cell receptor repertoire, with respect to diversity and frequency.

In the study, 6 pre-REP eTIL/rTIL pairs were harvested from the following histologies: ovarian cancer; renal cancer (n=2); and breast cancer (TNBC n=2, ER+PR+n=1). The cell pellets were shipped on dry ice to iRepertoire (Huntsville, Ala., USA) for RNA extraction and Vβ sequencing.

Figure 9:
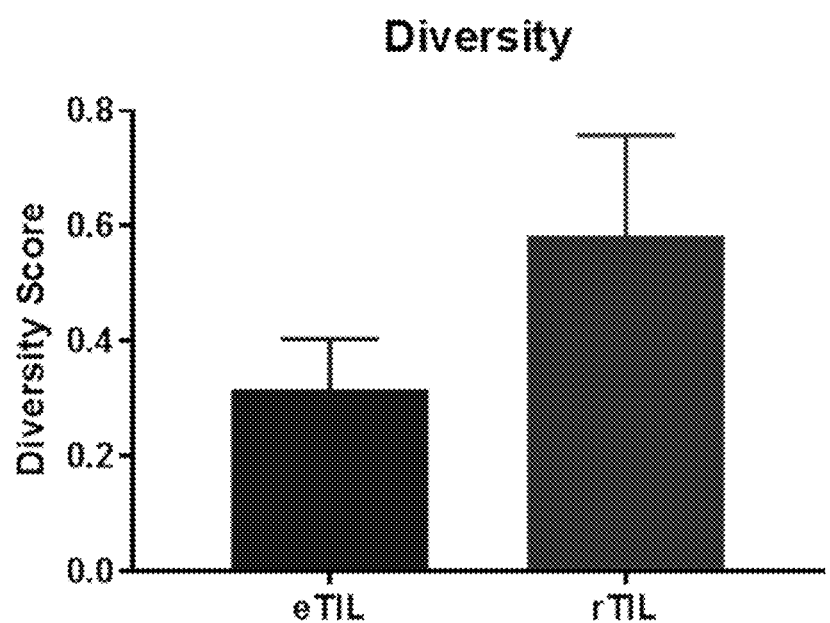
FIG. 9 illustrates the diversity of the TCRvβ repetoire (i.e., the diversity score) in eTIL and rTIL.
Figure 10:
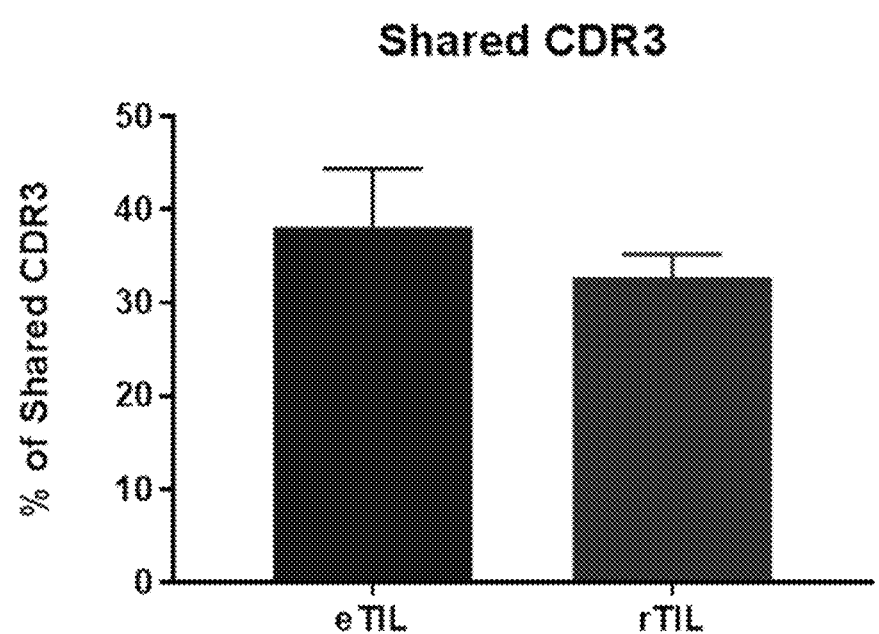
FIG. 10 illustrates the percent of shared CDR3s in eTIL and rTIL.
Figure 14:
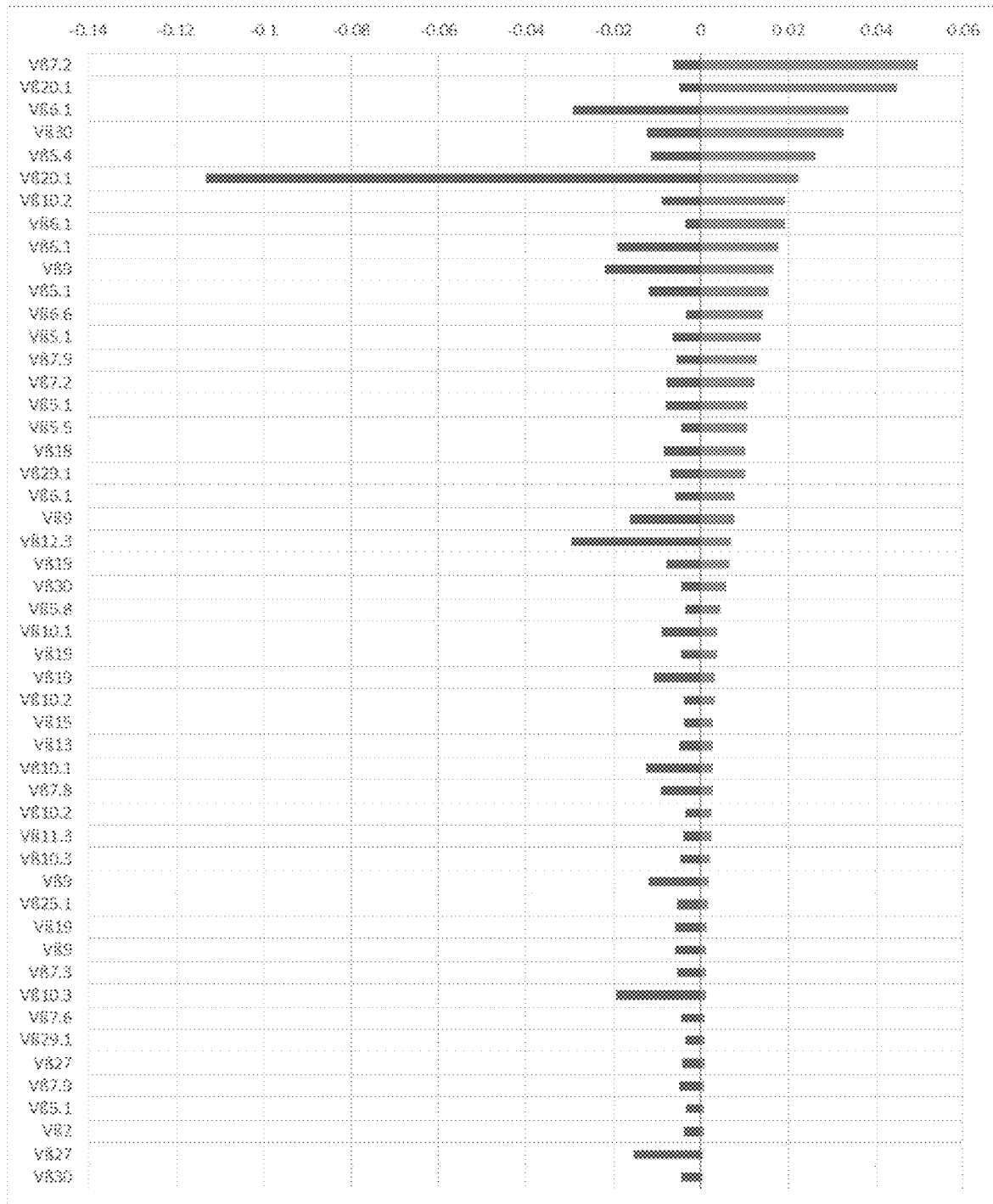
FIG. 14 illustrates a clonotype graph showing the top 50 shared CDR3s between eTIL and rTIL (for three eTIL/rTIL pairs) from ovarian carcinoma.
Figure 15:
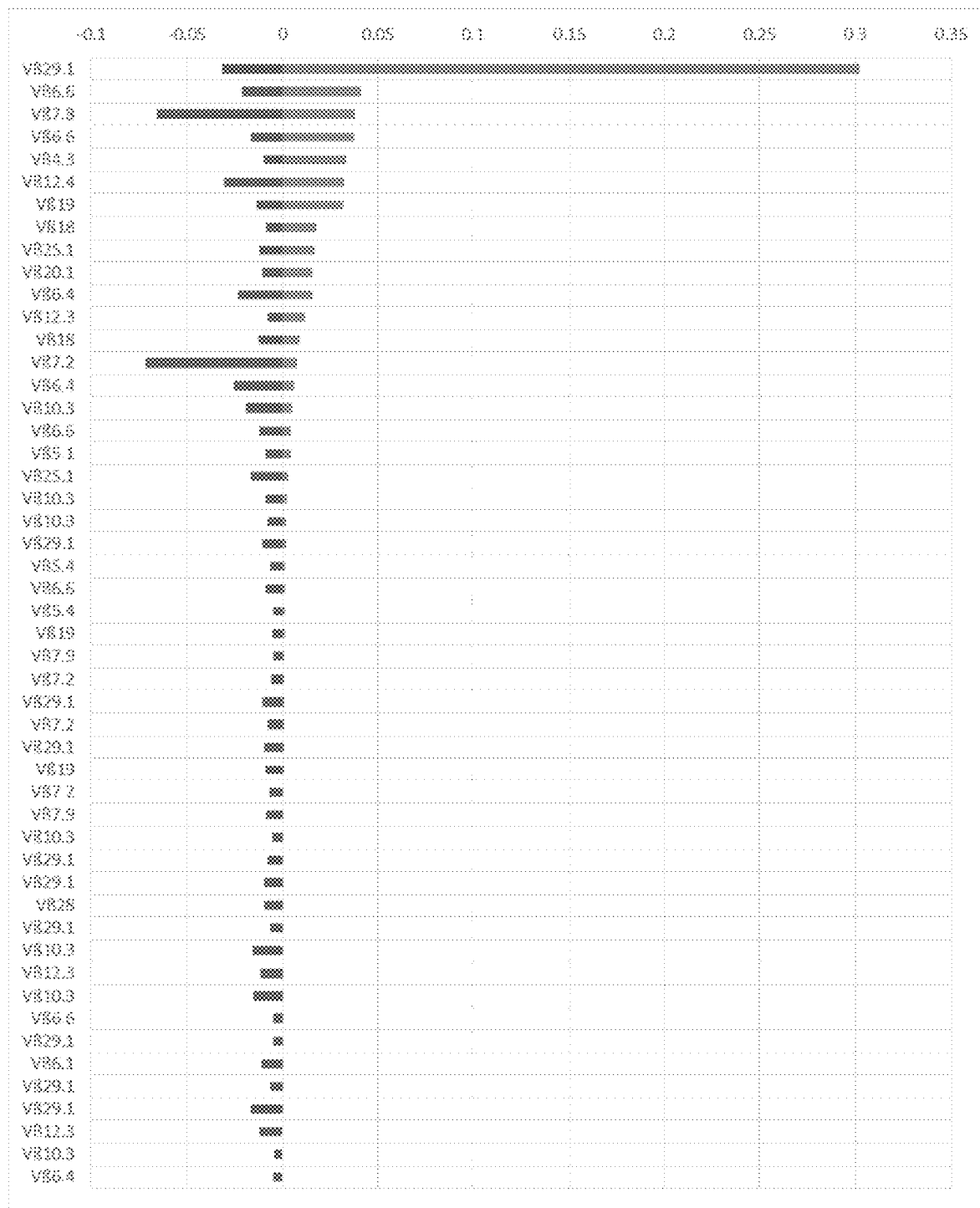
FIG. 15 illustrates a clonotype graph showing the top 50 shared CDR3s between eTIL and rTIL (for three eTIL/rTIL pairs) from renal carcinoma.
Figure 16:
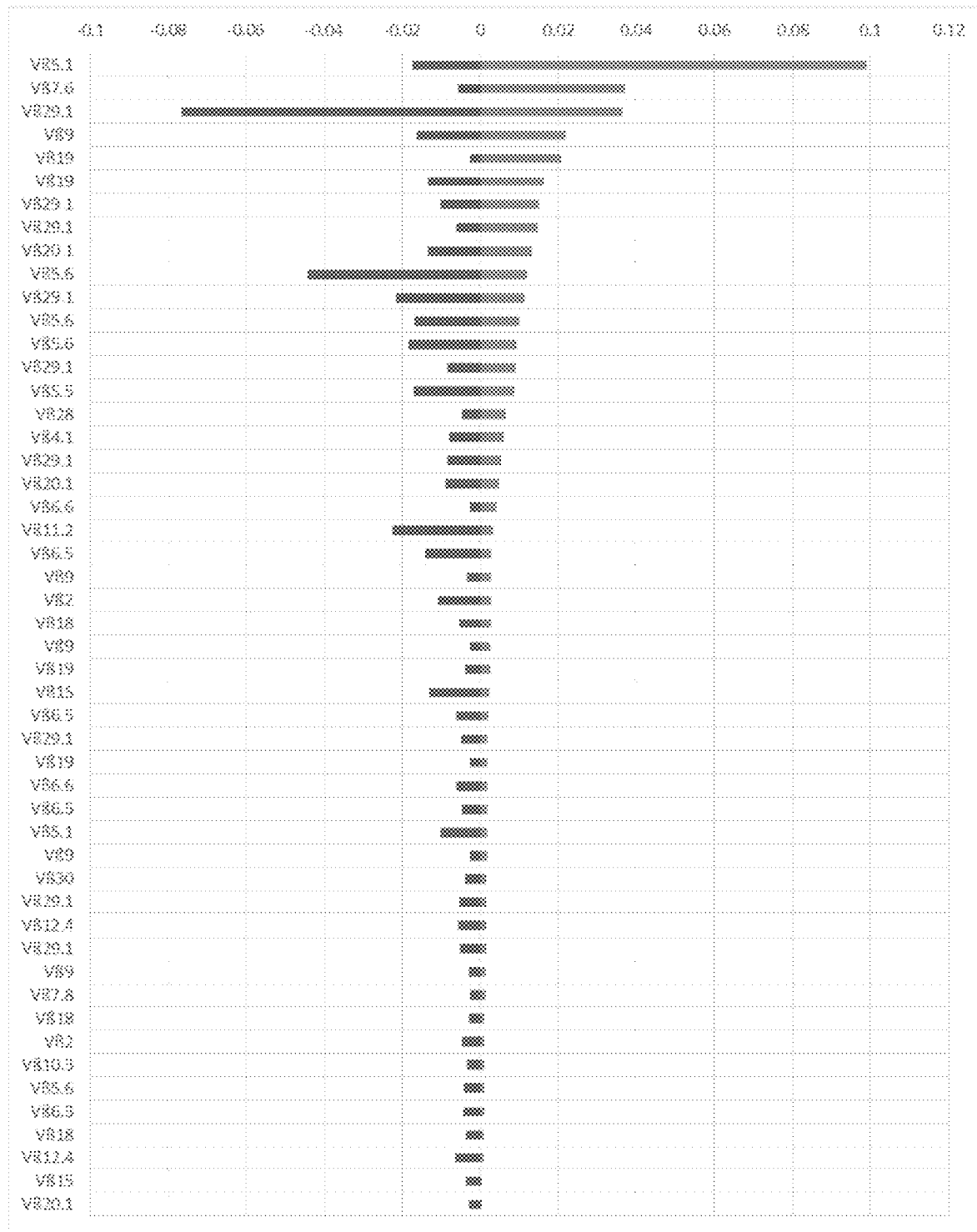
FIG. 16 illustrates a clonotype graph showing the top 50 shared CDR3s between eTIL and rTIL (for three eTIL/rTIL pairs) from triple negative breast carcinoma.

The results of this study are illustrated in FIGS. 9-10 and 14-16. In particular, FIGS. 9 and 10 illustrate the diversity score and the % of shared CDR3s, respectively. Furthermore, three clonotype graphs showing the top shared 50 CDR3s are shown in FIGS. 14, 15, and 16 for ovarian carcinoma, renal carcinoma, and triple negative breast carcinoma, respectively.

Surprisingly, the diversity of the TCRvβ repertoire is greater in the rTIL than in the eTIL (FIG. 9). Approximately 30-50% of the total CDR3 in the eTIL and rTIL are shared (FIG. 10), demonstrating that a large percentage of the total CDR3's are differentially expressed in the two populations. However, of the shared CDR3s the top 50 clones were mostly shared between the two populations, suggesting that eTIL and rTIL have clones with similar antigen specificity (see FIGS. 14-16). Moreover, the frequency of the top 50 clones varied, suggesting again that the eTIL and rTIL are surprisingly distinct T cell populations.

Example 7

Study of Co-Culture Proliferation Assays

The eTIL and rTIL were assessed determine whether the rTIL can alter the proliferation status of the eTIL, upon co-culture (or vice versa).

In the study, 5 pre-REP eTIL/rTIL pairs were harvested from the following histologies: renal cancer, triple-negative breast cancer (TNBC), melanoma, lung cancer, and colorectal cancer. The rTIL were isolated from the tumor remnants by a 60-min enzymatic digestion at 37° C. eTIL were stained with Cell Trace Yellow and rTIL with Cell Trace Red to independently track the two distinct populations. 1e6 of eTIL, 5e5 eTIL+5e5 rTIL, and 1e6 rTIL were cultured for 4 days at 37° C. with IL-2+/− and OKT3 (anti-CD3 antibody) and assessed for proliferation by flow cytometry.

Figure 11:
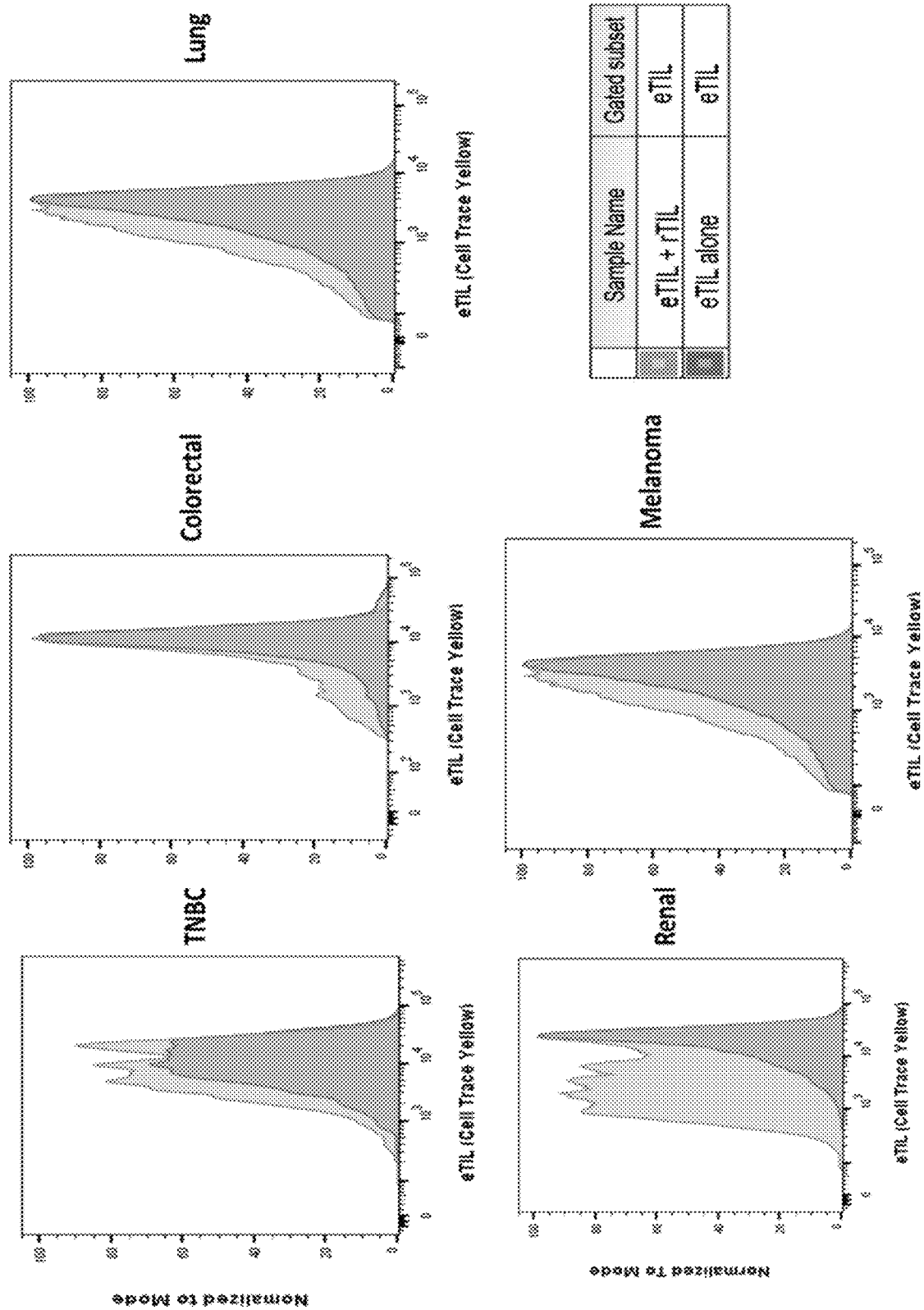
FIG. 11 illustrates cell proliferation analyses in triple negative breast carcinoma, colorectal carcinoma, lung carcinoma, renal carcinoma, and melanoma where eTIL from either the CD4+ or CD8+ population in all five tumors demonstrated an enhancement in the proliferative capacity upon co-culture with rTIL with anti-CD3 antibody as demonstrated by a shift (or dye dilution) in the Cell Trace dye, when compared to eTIL alone. The red represents the eTIL and the blue represents the eTIL when co-cultured with the rTIL.

The results of this study are illustrated in FIG. 11. In FIG. 11, the eTIL from either the CD4+ or CD8+ population in all five tumors demonstrated an enhancement in the proliferative capacity upon co-culture with rTIL with anti-CD3 antibody as demonstrated by a shift (or dye dilution) in the Cell Trace dye, when compared to eTIL alone. The red represents the eTIL and the blue represents the eTIL when co-cultured with the rTIL.

Example 8

Study of Co-Culture Proliferation Assays

The eTIL and rTIL were assessed identify similarities and/or differences in the gene expression profile of rTIL and eTIL.

In the study, Nanostring's nCounter technology was utilized, which employs a color-coded barcode multiplexed to mRNA to deliver a digital readout of gene expression. Purified RNA (RNeasy, Qiagen) from six matched eTIL and rTIL samples were hybridized with an nCounter Immunology V2 panel codeset for 16 hours on a thermocycler. Codesets consist of a mixture of capture and reporter probes that are multiplexed with the target RNA through 22 bp interactions during thermocycling. Samples were loaded into a 12-well SPRINT cartridge and ran on an nCounter SPRINT device. Count data are exported in a custom RCC format and matched to an RLF file which matches gene names to probe IDs. Normalization and analysis were done on nSolver 3.0 (NanoString Technologies, Inc.).

Figure 12:
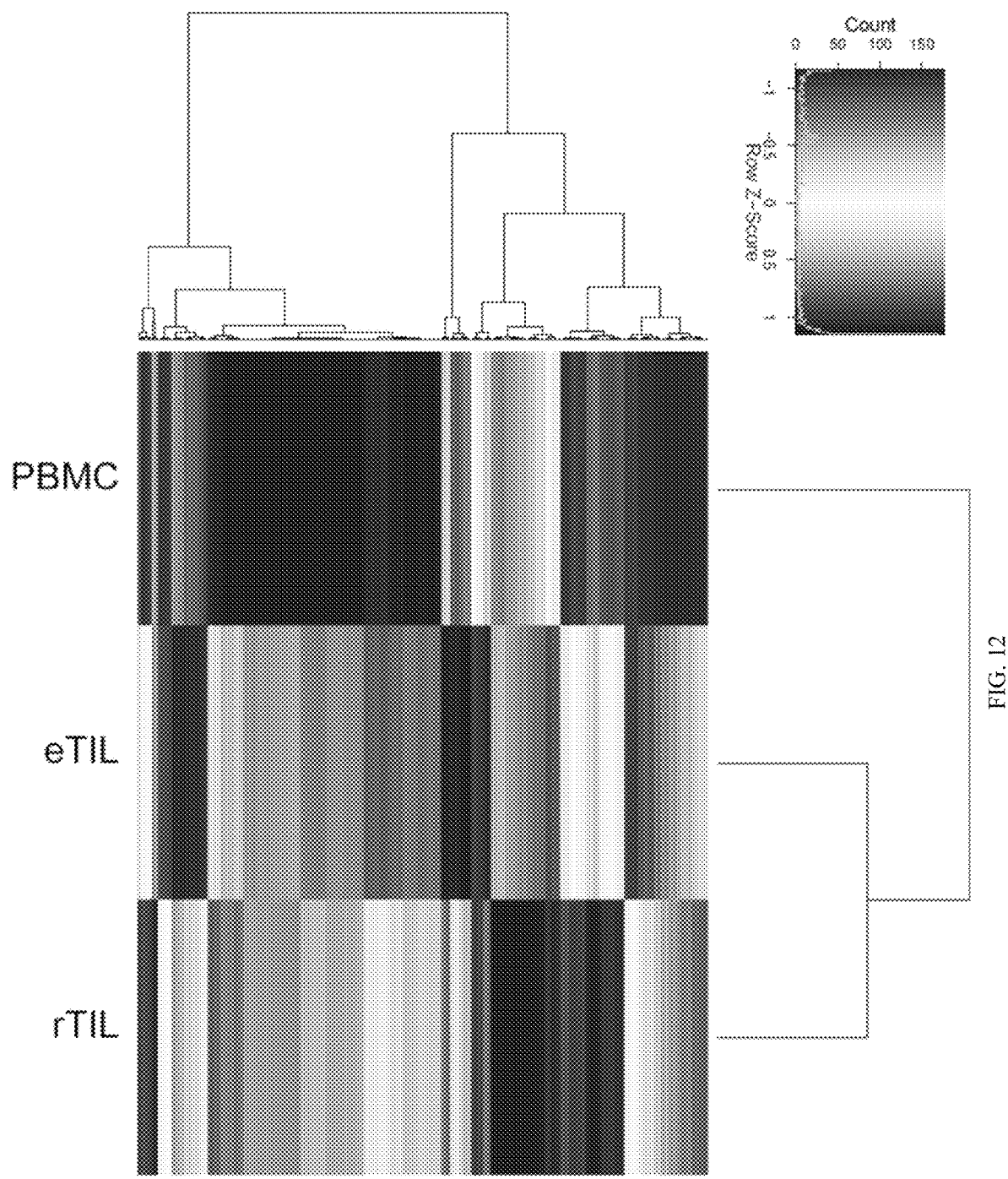
FIG. 12 illustrates a heat map prepared from a Nanostring analysis, which shows that the gene expression profile for eTIL and rTIL is significantly different.
Figure 13:
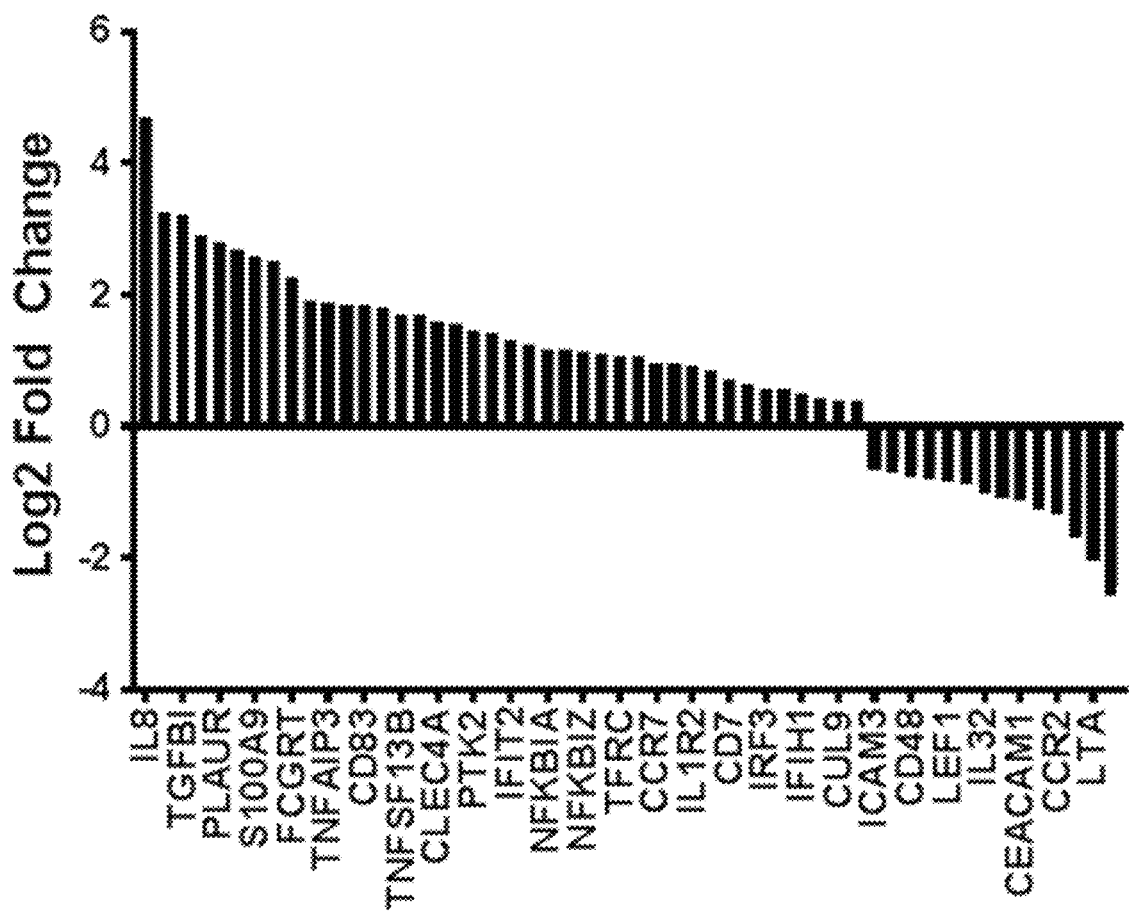
FIG. 13 illustrates a graph prepared from a Nanostring analysis, which shows that several genes are significantly upregulated or downregulated in the rTIL as compared to the eTIL.

The results of this study are illustrated in FIGS. 12 and 13. As shown in FIGS. 12 and 13, the gene expression profile is significantly different when comparing the eTIL and rTIL (see the heat map in FIG. 12). There are several genes that are significantly upregulated or downregulated in the rTIL compared to the eTIL (FIG. 13).

We claim:

1. A method of treating a cancer in a patient in need of such treatment, the method comprising:
   obtaining a therapeutically effective amount of remnant tumor infiltrating lymphocytes (rTILs), by enzymatically digesting tumor remnants separated from emergent tumor infiltrating lymphocytes (eTILs) using a digest mixture comprising a deoxyribonuclease, a collagenase, a hyaluronidase, or a combination thereof, and expanding the rTILs with a second cell culture medium comprising cell culture media, irradiated feeder cells, OKT-3 antibody, and interleukin 2 (IL-2), wherein the tumor remnants and the eTILs are derived from tumor tissue that was obtained from the patient, fragmented and treated with a first cell culture medium comprising IL-2,
   and administering the therapeutically effective amount of rTILs to the patient.

2. The method of claim 1, wherein the tumor tissue is selected from the group consisting of melanoma tumor tissue, head and neck tumor tissue, breast tumor tissue, renal tumor tissue, pancreatic tumor tissue, glioblastoma tumor tissue, lung tumor tissue, colorectal tumor tissue, sarcoma tumor tissue, triple negative breast tumor tissue, cervical tumor tissue, ovarian tumor tissue, and acute myeloid leukemia bone marrow or tumor tissue.

3. The method of claim 1, wherein the irradiated feeder cells comprise irradiated allogeneic peripheral blood mononuclear cells.

4. The method of claim 1, wherein IL-2 is present in the second cell culture medium at an initial concentration of about 3000 IU/mL and OKT-3 antibody is present in the second cell culture medium at an initial concentration of about 30 ng/mL.

5. The method of claim 1, wherein $CD56^+$ expression in the rTILs is reduced by at least 3-fold relative to $CD56^+$ expression in the eTILs.

6. The method of claim 1, wherein $CD69^+$ expression in the rTILs is increased by at least 2-fold relative to $CD69^+$ expression in the eTILs.

7. The method of claim 1, wherein the first cell culture medium further comprises a cytokine selected from the group consisting of IL-4, IL-7, IL-15, IL-21, and combinations thereof.

8. The method of claim 1, wherein the second cell culture medium further comprises a cytokine selected from the group consisting of IL-4, IL-7, IL-15, IL-21, and combinations thereof.

9. The method of claim 1, wherein the rTILs are cryopreserved prior to obtaining the rTILs.

10. The method of claim 9, further comprising the step of thawing the cryopreserved rTILs prior to obtaining the rTILs.

11. The method of claim 1, further comprising the steps of:
    administering a non-myeloablative lymphodepletion regimen to the patient prior to administering of the therapeutically effective amount of rTILs to the patient; and
    administering a high-dose IL-2 regimen to the patient starting on the day after administering of the therapeutically effective amount of rTILs to the patient.

12. The method of claim 11, wherein a therapeutically effective amount of eTILs is simultaneously obtained in a mixture with the therapeutically effective amount of rTILs.

13. The method of claim 11, wherein the non-myeloablative lymphodepletion regimen comprises the steps of administering cyclophosphamide to the patient at a dose of 60 mg/m2/day for two days followed by administering fludarabine to the patient at a dose of 25 mg/m2/day for five days.

14. The method of claim 11, wherein the high-dose IL-2 regimen comprises 600,000 or 720,000 IU/kg of aldesleukin, or a biosimilar or variant thereof, administered to the patient as a 15-minute bolus intravenous infusion every eight hours until tolerance.

15. The method of claim 1, wherein the cancer is selected from the group consisting of melanoma, double-refractory melanoma, uveal melanoma, ovarian cancer, cervical cancer, lung cancer, bladder cancer, breast cancer, head and neck cancer, renal cell carcinoma, acute myeloid leukemia, colorectal cancer, and sarcoma.

16. The method of claim 15, wherein the cancer is breast cancer, and wherein the breast cancer is selected from the group consisting of triple negative breast cancer, estrogen receptor-positive breast cancer, progesterone receptor-positive breast cancer, and estrogen receptor-positive/progesterone receptor-positive breast cancer.

17. The method of claim 15, wherein the cancer is lung cancer, and the lung cancer is selected from the group consisting of non-small cell lung cancer and small cell lung cancer.

18. The method of claim 1, wherein the therapeutically effective amount of rTILs is provided in a pharmaceutical composition, wherein the concentration of the rTILs in the pharmaceutical composition is greater than 50%.

* * * * *